United States Patent
Dana et al.

(10) Patent No.: US 7,918,867 B2
(45) Date of Patent: *Apr. 5, 2011

(54) SUTURE TRIMMER

(75) Inventors: Michael Dana, Newark, CA (US); T. Daniel Gross, Los Gatos, CA (US); Maurice Marthaler, Santa Rosa, CA (US); Dawn Ma, San Jose, CA (US); Steven C. Anderson, Mountain View, CA (US); Marc Terwilliger, Palo Alto, CA (US); Jim Swett, Livermore, CA (US); Mitchell B. Friedman, Buffalo Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 1322 days.

This patent is subject to a terminal disclaimer.

(21) Appl. No.: 10/324,730

(22) Filed: Dec. 19, 2002

(65) Prior Publication Data

US 2003/0181926 A1    Sep. 25, 2003

Related U.S. Application Data

(63) Continuation-in-part of application No. 10/004,817, filed on Dec. 7, 2001, now Pat. No. 6,746,457, and a continuation-in-part of application No. 10/027,681, filed on Dec. 21, 2001.

(51) Int. Cl.
*A61B 17/04* (2006.01)
*A61B 17/12* (2006.01)

(52) U.S. Cl. ......... 606/144; 606/139; 606/145; 606/148

(58) Field of Classification Search .......... 606/144, 606/148, 167, 170, 171, 232
See application file for complete search history.

(56) References Cited

U.S. PATENT DOCUMENTS

| | | |
|---|---|---|
| 3,328,876 A | 7/1967 | Hoppe |
| 3,372,477 A | 3/1968 | Hoppe |
| 3,380,448 A | 4/1968 | Sadove et al. |
| 3,625,556 A | 12/1971 | Stromberg |
| 3,752,516 A | 8/1973 | Mumma |
| 3,840,017 A | 10/1974 | Violante |
| 4,246,698 A | 1/1981 | Lasner et al. |
| 4,369,787 A | 1/1983 | Lasner et al. |
| 4,527,331 A | 7/1985 | Lasner et al. |
| 4,602,635 A | 7/1986 | Mulhollan |

(Continued)

FOREIGN PATENT DOCUMENTS

DE    9112301    1/1992

(Continued)

OTHER PUBLICATIONS

PCT/US02/39151 International Search Report.

(Continued)

*Primary Examiner* — Todd E Manahan
*Assistant Examiner* — Michael G. Mendoza
(74) *Attorney, Agent, or Firm* — Workman Nydegger

(57) ABSTRACT

A suture trimmer having a shaft with a groove formed in the side thereof, a cutting member movably disposed within the shaft, and a suture retainer slidably disposed within the shaft. The suture trimmer may be used to position knots formed within a suture loop prior to trimming the free end(s) of the suture loop, and to deliver an agent near the location where the suture is severed.

39 Claims, 34 Drawing Sheets

U.S. PATENT DOCUMENTS

| | | |
|---|---|---|
| 4,641,652 A | 2/1987 | Hatterer |
| 4,957,498 A | 9/1990 | Caspari et al. |
| 4,961,741 A | 10/1990 | Hayhurst |
| 5,059,201 A | 10/1991 | Asnis |
| 5,133,723 A | 7/1992 | Li |
| 5,176,691 A | 1/1993 | Pierce |
| 5,176,695 A | 1/1993 | Dulebohn |
| 5,242,459 A | 9/1993 | Buelna |
| 5,269,791 A | 12/1993 | Mayzels et al. |
| 5,292,327 A | 3/1994 | Dodd et al. |
| 5,304,190 A | 4/1994 | Reckelhoff et al. |
| 5,312,423 A | 5/1994 | Rosenbluth et al. |
| 5,342,459 A | 8/1994 | Klemp et al. |
| 5,403,330 A | 4/1995 | Tuason |
| 5,405,351 A | 4/1995 | Kinet |
| 5,405,354 A | 4/1995 | Sarrett |
| 5,417,699 A | 5/1995 | Klein et al. |
| 5,423,837 A | 6/1995 | Mericle et al. |
| 5,462,562 A | 10/1995 | Elkus |
| 5,520,702 A | 5/1996 | Sauer et al. |
| 5,527,322 A | 6/1996 | Klein et al. |
| 5,549,618 A | 8/1996 | Fleenor et al. |
| 5,565,122 A | 10/1996 | Zinnbauer et al. |
| 5,585,122 A | 12/1996 | Drum et al. |
| 5,643,289 A | 7/1997 | Sauer et al. |
| 5,649,939 A | 7/1997 | Reddick |
| 5,669,917 A | 9/1997 | Sauer et al. |
| 5,704,943 A | 1/1998 | Yoon |
| 5,746,752 A | 5/1998 | Burkhart |
| 5,797,928 A | 8/1998 | Kogasaka |
| 5,797,929 A | 8/1998 | Andreas et al. |
| 5,830,234 A | 11/1998 | Wojciechowicz et al. |
| 5,860,993 A | 1/1999 | Thompson |
| 5,879,371 A | 3/1999 | Gardiner et al. |
| 5,997,555 A | 12/1999 | Kontos |
| 6,004,295 A | 12/1999 | Langer et al. |
| 6,007,544 A | 12/1999 | Kim |
| 6,007,554 A | 12/1999 | Van Ess |
| 6,045,570 A | 4/2000 | Epstein |
| 6,051,004 A | 4/2000 | Gill |
| 6,077,279 A | 6/2000 | Kontos |
| 6,090,063 A | 7/2000 | Makower et al. |
| 6,132,439 A | 10/2000 | Kontos |
| 6,171,317 B1 | 1/2001 | Jackson et al. |
| 6,254,620 B1 | 7/2001 | Koh |
| 6,261,272 B1 | 7/2001 | Gross et al. |
| 6,527,785 B2 | 3/2003 | Sancoff et al. |
| 6,620,185 B1 * | 9/2003 | Harvie et al. ............... 606/232 |
| 6,733,509 B2 | 5/2004 | Nobles |
| 6,746,457 B2 | 6/2004 | Dana et al. |
| 6,860,890 B2 | 3/2005 | Bachman |
| 7,094,246 B2 | 8/2006 | Anderson |
| 7,147,646 B2 | 12/2006 | Dana et al. |
| 2002/0087178 A1 | 7/2002 | Nobles |
| 2002/0123758 A1 | 9/2002 | Bachman |
| 2003/0120287 A1 | 6/2003 | Nobles |
| 2006/0264977 A1 | 11/2006 | Dana |
| 2006/0293700 A1 | 12/2006 | Dana |

FOREIGN PATENT DOCUMENTS

| | | |
|---|---|---|
| DE | 9214580 | 4/1994 |
| EP | 0669103 | 8/1995 |
| WO | 94/08515 | 4/1994 |
| WO | WO 95/32669 | 12/1995 |
| WO | 00/69342 | 5/2000 |
| WO | 02/15795 | 8/2001 |
| WO | WO 03/049621 | 6/2003 |
| WO | WO 03/059174 | 7/2003 |

OTHER PUBLICATIONS

Patent No. 6,746,457, Office Action, mailed Dec. 18, 2002.
Patent No. 6,746,457, Notice of Allowance, mailed Jul. 28, 2003.
Patent No. 6,746,457, Notice of Allowance, mailed Feb. 4, 2004.
Patent No. 6,746,457, Issue Notification, mailed May 20, 2004.
Patent No. 7,094,246, Office Action, mailed Aug. 31, 2005.
Patent No. 7,094,246, Notice of Allowance, mailed Feb. 23, 2006.
Patent No. 7,094,246, Issue Notification, mailed Aug. 2, 2006.
Patent No. 7,147,646, Office Action, mailed May 17, 2006.
Patent No. 7,147,646, Notice of Allowance, mailed Oct. 2, 2006.
Patent No. 7,147,646, Issue Notification, mailed Nov. 22, 2006.
Patent No. 2003/0120287, Office Action, mailed Jun. 2, 2003.
Patent No. 2003/0120287, Office Action, mailed Dec. 8, 2003.
Patent No. 2003/0120287, Office Action, mailed May 28, 2004.
Patent No. 2003/0120287, Office Action, mailed Oct. 23, 2006.
Patent No. 2003/0120287, Office Action, mailed Apr. 17, 2007.
U.S. Appl. No. 10/027,681, mailed May 27, 2008, Office Action.
U.S. Appl. No. 10/027,681, mailed Dec. 23, 2008, Office Action.
U.S. Appl. No. 10/027,681, mailed Jul. 8, 2009, Office Action.
U.S. Appl. No. 11/461,243, mailed Apr. 29, 2009, Office Action.
U.S. Appl. No. 11/461,243, mailed Oct. 21, 2009, Office Action.
U.S. Appl. No. 11/465,035, mailed Nov. 28, 2008, Office Action.
U.S. Appl. No. 10/027,681, mailed Feb. 17, 2010, Office Action.
U.S. Appl. No. 11/465,035, mailed Mar. 4, 2010, Office Action.
U.S. Appl. No. 11/461,243, mailed Mar. 15, 2010, Office Action.
U.S. Appl. No. 11/461,243, mailed Jul. 28, 2010, Notice of Allowance.
U.S. Appl. No. 11/465,035, mailed Jun. 22, 2010, Office Action.
U.S. Appl. No. 10/027,681, mailed Aug. 16, 2010, Office Action.

* cited by examiner

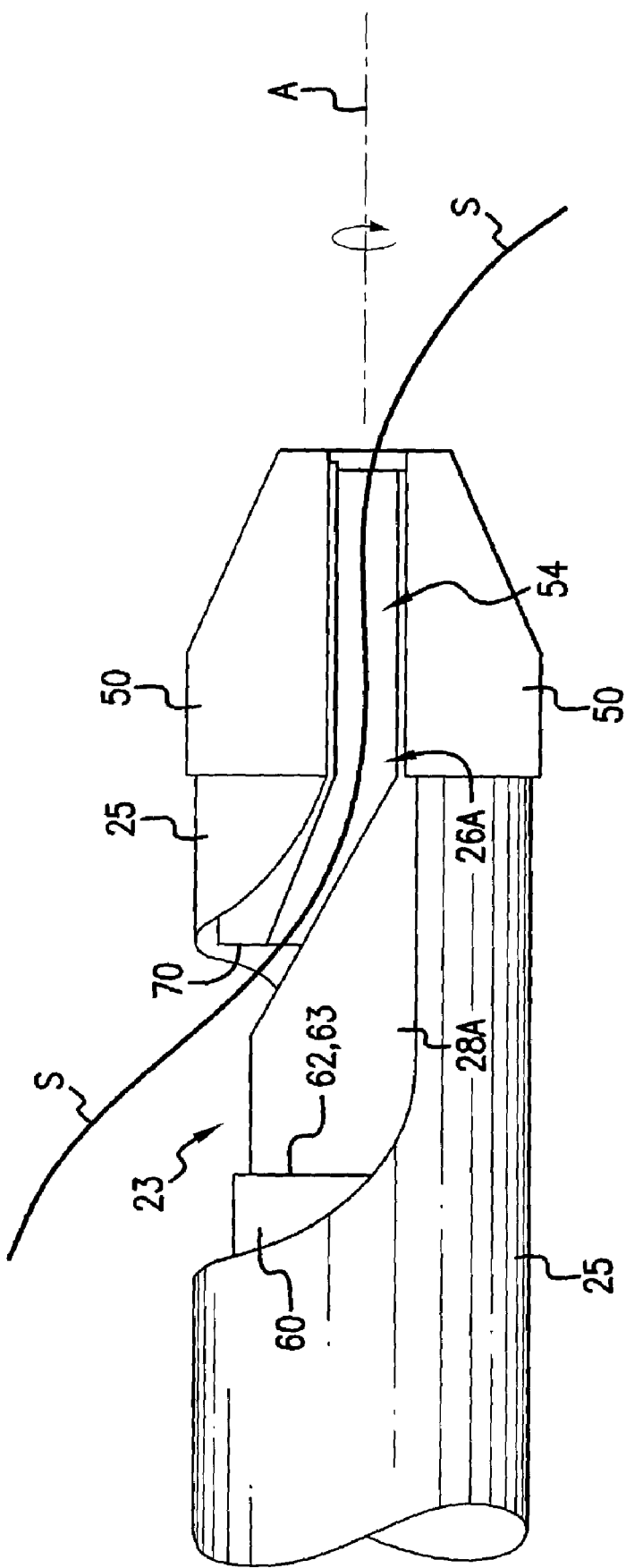

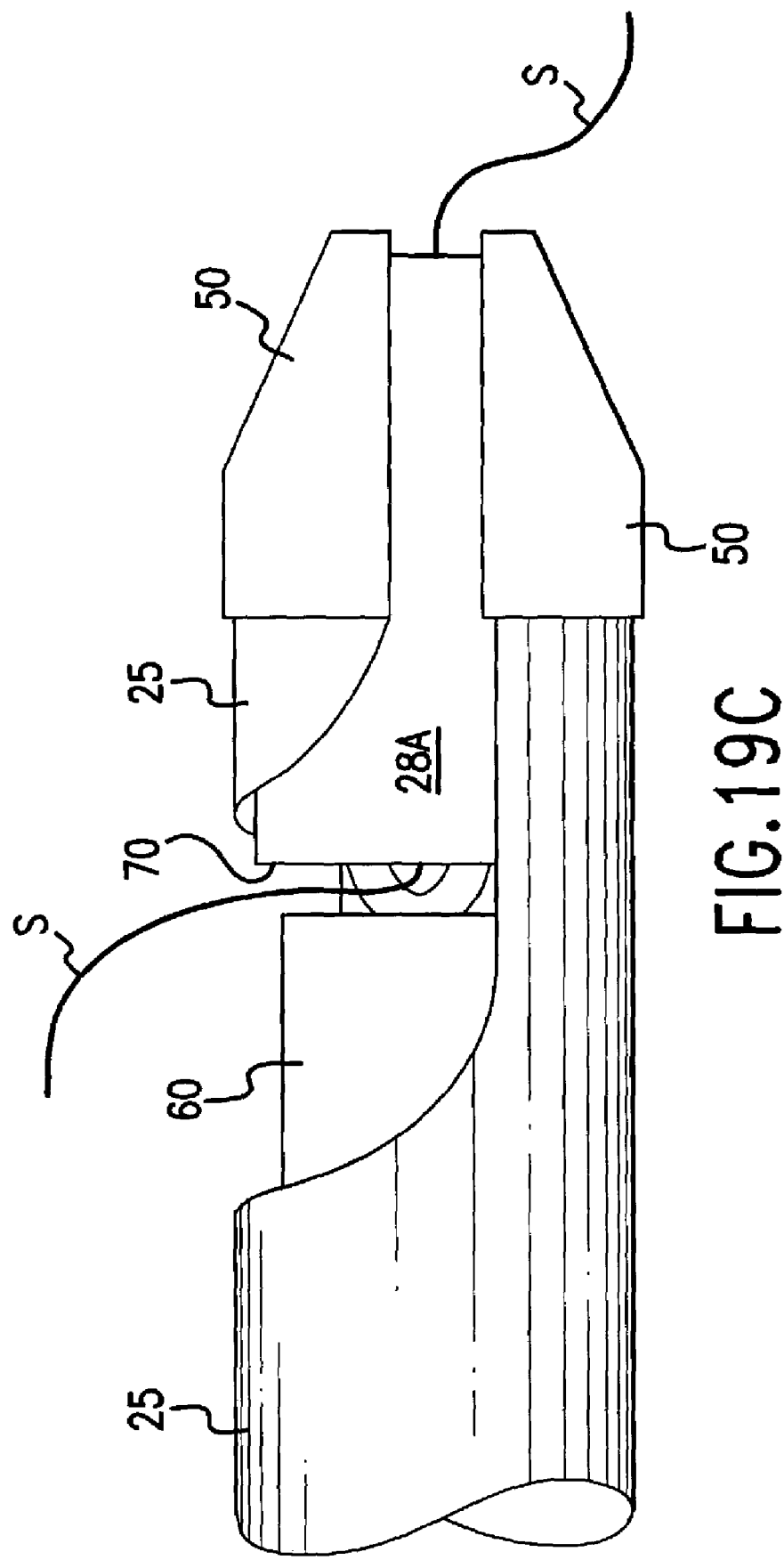

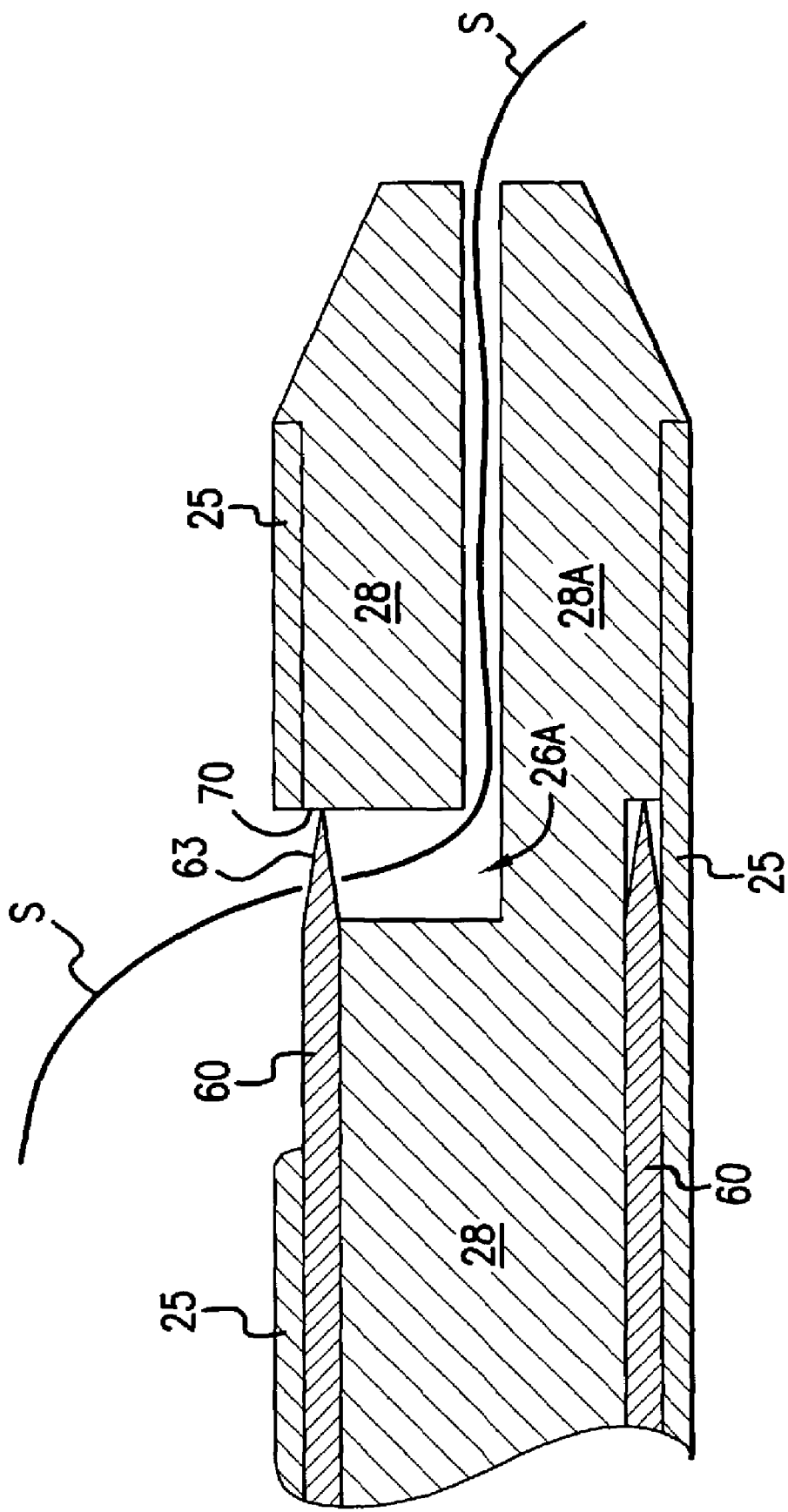

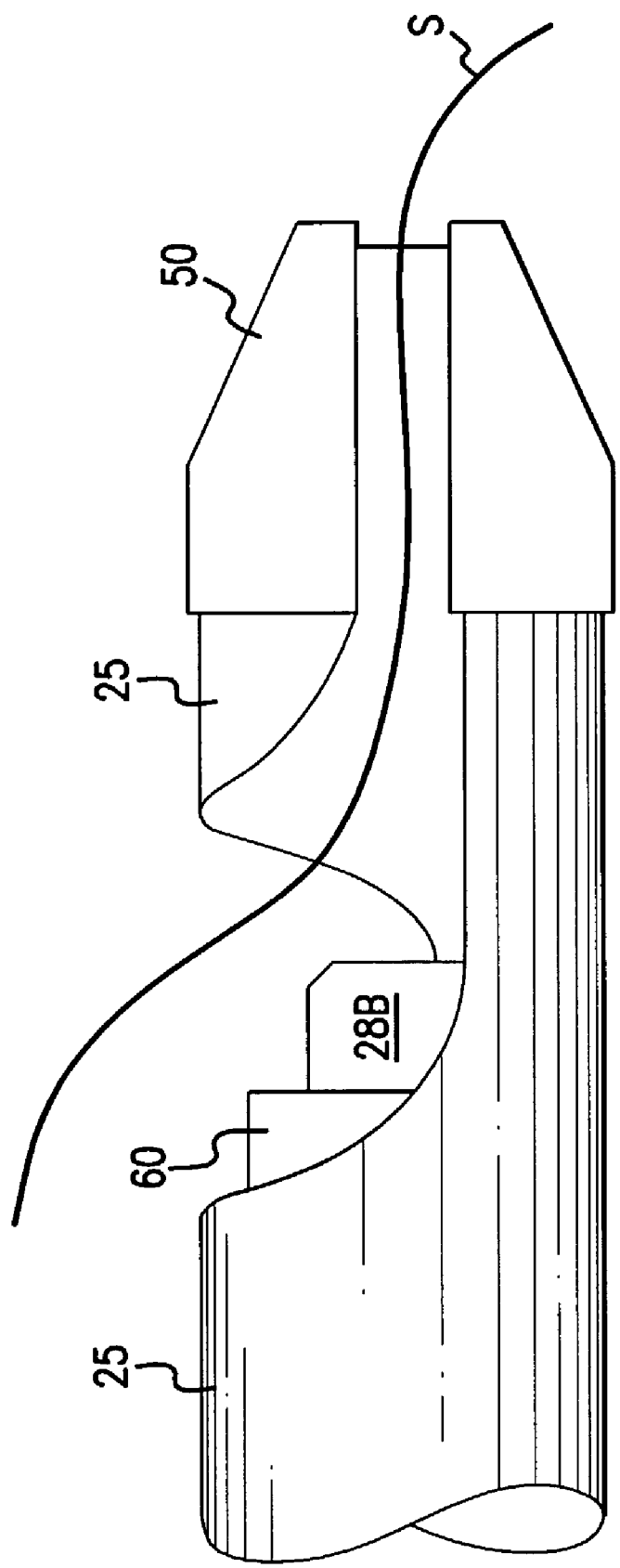

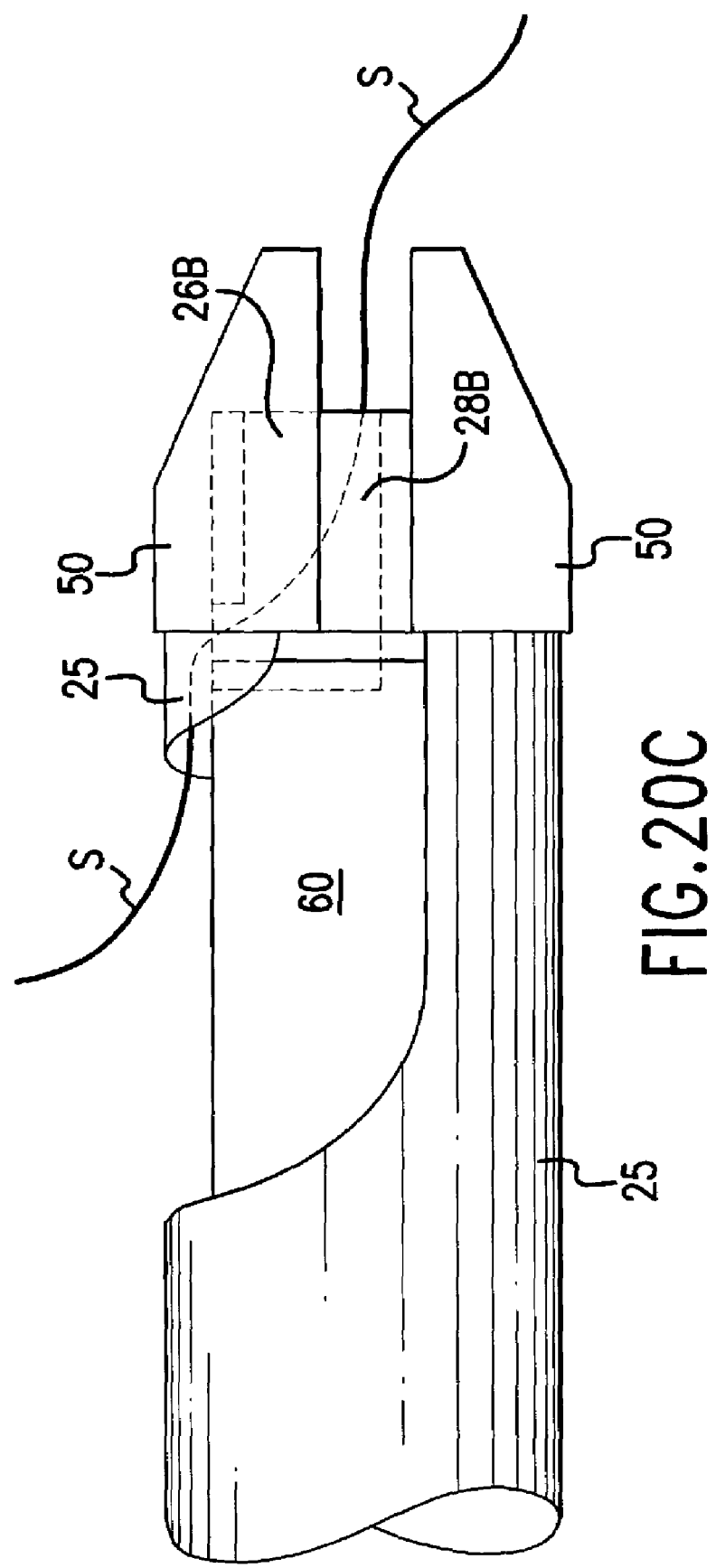

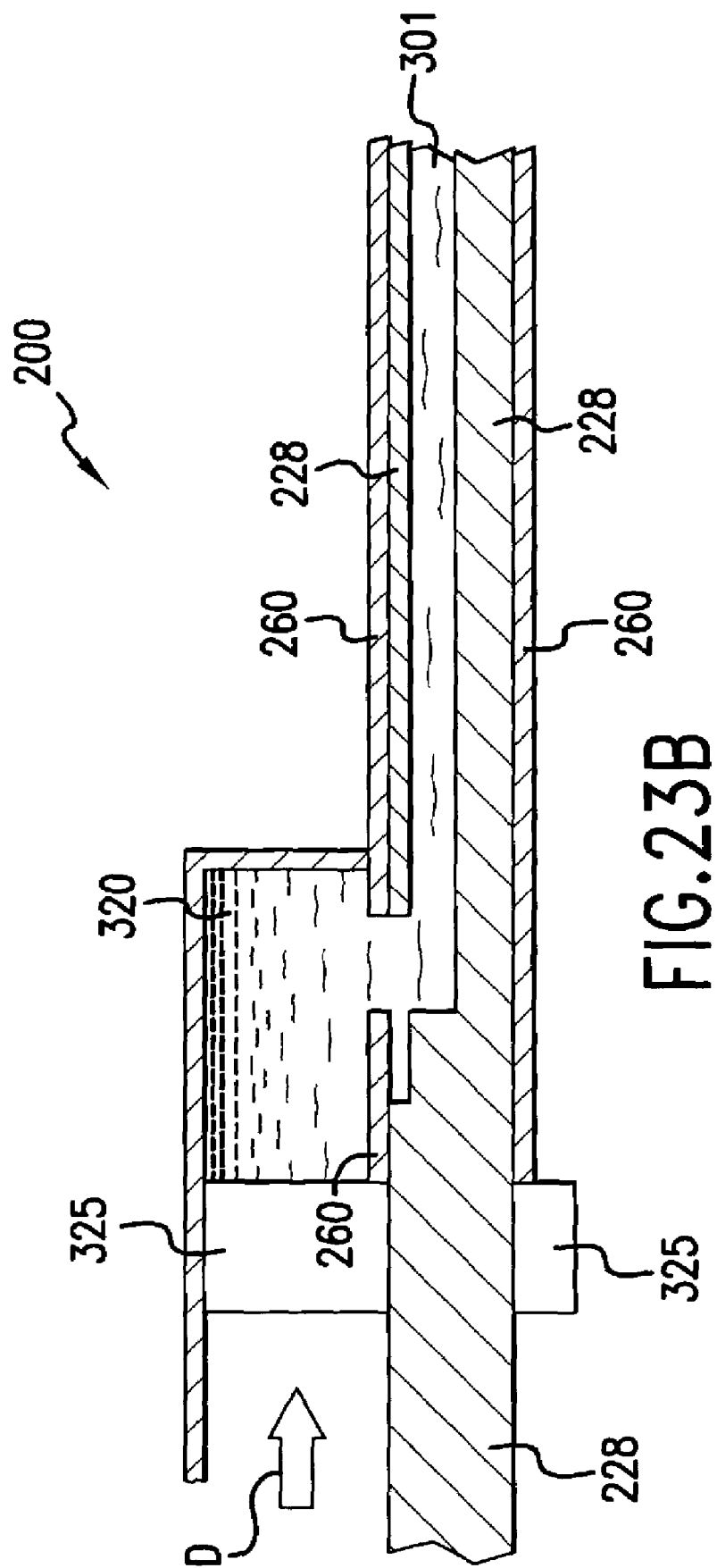

SUTURE TRIMMER

RELATED APPLICATIONS

The present application is a continuation-in-part of pending U.S. patent application Ser. No. 10/004,817, filed Dec. 7, 2001, now U.S. Pat. No. 6,746,457 and is also a continuation-in-part of pending U.S. patent application Ser. No. 10/027,681, filed Dec. 21, 2001, the complete disclosures of which are incorporated herein by reference in their entirety.

FIELD OF THE INVENTION

The present invention relates generally to surgical devices and methods. More particularly, the present invention relates to the construction and use of devices for advancing surgical knot(s) and trimming the ends of the suture adjacent to the knot(s). Such a device is to be referred to as a "suture trimmer", as used through the appended specification.

BACKGROUND OF THE INVENTION

The closing of incisions and wounds using suture is a preferred technique of surgeons and many other physicians. While other techniques are now available such as stapling, the use of "tissue glues," and the use of collagen for closing vascular punctures, the use of suture is often preferred because it provides a reliable and tight closure of any wound. Additionally, if a suture is to fail, the surgeon will know immediately. In contrast, many of the other devices listed above which may not fail until some time after the procedure.

While the suturing of a wound is a relatively straightforward procedure in most open surgical procedures, placement and tying of sutures in laprascopic and other minimally invasive procedures can be problematic. In order to provide for suturing under such circumstances, a variety of devices have been developed for the remote placement and tying of suture through cannulas under video observation. Usually, a sliding knot will be formed in a suture loop, a tool known as a "knot pusher" such as that shown in U.S. Pat. No. 5,797,929 the entirety of which is hereby incorporated by reference, is utilized to advance and position the knot and tighten the loop of suture.

Such knot pushing devices may also be utilized in recently developed techniques for the remote suturing of vascular punctures. Punctures may be formed in the femoral or other arteries to provide vascular access for performing angioplasty and other vascular procedures. Such techniques are described in U.S. Pat. Nos. 5,417,699; 5,527,322 and 6,136,010 the entirety of which are hereby incorporated by reference. Such methods result in the placement of a suture loop through tissue on opposite sides of the vascular puncture. Two free ends of the suture loop are brought out through a tissue tract leading to the puncture, and the ends may be externally tied by the treating physician. Alternatively, a knot forming device such as that shown in U.S. Pat. No. 6,171,317, the entirety of which is hereby incorporated by reference, may be utilized to tie a knot.

Through the use of a knot pusher, such as that shown and described in U.S. Pat. No. 5,797,929 the knot may be advanced through the tissue tract so that it lies directly over the adventitial wall of the blood vessel.

After the knot has been advanced over the adventitial wall of the blood vessel and tightened, the excess suture must be cut away. Typically, a surgeon may utilize a scalpel or a pair of scissors to cut the suture ends just below the exterior surface of the patient's skin.

A concern with this method is that by leaving lengths of suture within the wound may lead to irritation of the incision. More significantly, a relatively long suture end, extending from the knot at the vessel repair to the skin level, may act as a "wick" for infective microorganisms which may be present at skin level. The wick would provide a conduit for these microorganisms to travel from the skin surface to the vessel repair, thereby leading to infection. Many times a surgeon cannot easily shorten this cut length because the location of the knot is well below the patient's tissue and is not readily visible, therefore they can only shorten the suture to the point that they can visually see. Further still, many surgical procedures are moving away from being open and toward being minimally invasive wherein the procedure is performed within a small opening formed in the patient's tissue. As described above, many times the surgeon cannot see the vessel which they are trying to close with the suture.

Therefore there is a need for a device that will enable a surgeon to advance a knot and trim the excess suture from the knot without having to visually see the knot.

SUMMARY OF THE INVENTION

In accordance with the present invention there is provided a suture trimmer, the suture trimmer including a shaft having a proximal end and a distal end and an axis therebetween, the shaft having a slot formed in the side thereof, the slot in communication with an opening formed in the side of the shaft, the opening disposed proximal the distal end. In various embodiments, the suture trimmer may preferably include a cutting member that is slidably disposed within the shaft, and a suture retainer movably disposed within the shaft. As will be explained, the suture retainer may either be slidably or rotatable disposed within the shaft. Preferably, the suture retainer is disposed within the bore of the cutting member, but the present invention is not so limited.

In alternative embodiments, the cutting member may either be moved in a distal or proximal direction within the shaft of the suture trimmer to cut the suture(s).

In alternative embodiments, the suture is positioned within the groove and opening in the side of the shaft by either first moving the suture retainer in a proximal direction within the shaft or by rotating the suture retainer within the shaft.

In optional embodiments, the present invention is further adapted to dispense an agent at a location near or adjacent to where the suture is severed (for example, at or near the distal end of the shaft). Such agent may comprise an antibacterial or anti-infectant agent or a coagulant, but the present invention is not so limited. Rather, any suitable therapeutic agent may be dispensed by the present invention. Various systems for dispensing the agent may include, for example, a lumen passing through the device, an agent storage chamber on or within the device, or a removable agent storage cartridge received into the device.

Various exemplary structures or methods for cutting suture may include: (1) cutting the suture between the distal end of the cutting member and an anvil portion of the suture retainer; or (2) cutting suture between the distal end of the cutting member and a proximal end or flat face of a fitting received in the distal end of the shaft.

In accordance with another aspect of the present invention there is provided a method for trimming suture, the method including the steps of disposing a free end of suture through a groove and opening formed in a distal end of a suture trimmer, wherein a cutting member is actuated within the suture trimmer, the cutting member configured to sever the suture disposed in the opening. Preferably, such suture comprises a suture loop including at least one knot and at least one free end of suture. In one exemplary application, the method is performed by placing the suture loop through a wall of a patient's femoral artery, cutting the suture in a tissue tract adjacent to the femoral artery, and delivering an agent to the tissue tract in the vicinity of the loop of suture.

BRIEF DESCRIPTION OF THE DRAWINGS

The objects and advantages of the invention will become apparent from the following detailed description of preferred embodiments thereof in connection with the accompanying drawings in which like numerals designate like elements and in which:

FIG. 19A is a side elevation view of an embodiment of the invention using a rotating suture retainer and a push-to-cut cutting member, with the suture retainer rotated to a first position to receive a suture into a groove and opening in the device;

FIG. 19C is a view similar to FIG. 19B, but with the cutting member distally advanced to sever the suture;

FIG. 19D is a sectional side elevation view corresponding to FIG. 19C, further illustrating details of the operation of the system;

FIG. 20A is a side elevation view of an embodiment of the invention using a slidable suture retainer and a push-to-cut cutting member, with the suture retainer moved distally (i.e. retracted) to receive a suture into the device;

FIG. 20C is a view similar to FIG. 20B, but with the cutting member moved distally to sever the suture;

FIG. 23B is an enlarged view of a portion of the device shown in FIG. 22 after the agent has been dispensed;

DETAILED DESCRIPTION OF THE DRAWINGS

In accordance with the present invention there is provided a suture trimmer, the suture trimmer may be utilized by physicians in any of a variety of surgical procedures where suture loop has been formed in tissue to close an incision or wound, or for any other purpose. A slidable knot may be formed in the suture loop, and the suture trimmer may then be used to engage and advance the knot over a free end of the suture to close the suture loop. The knot can then be tightened by pulling on the other free end of the suture. The free ends of the suture may then be trimmed adjacent to the knot by actuating the cutting member of the suture trimmer.

Figure 1:
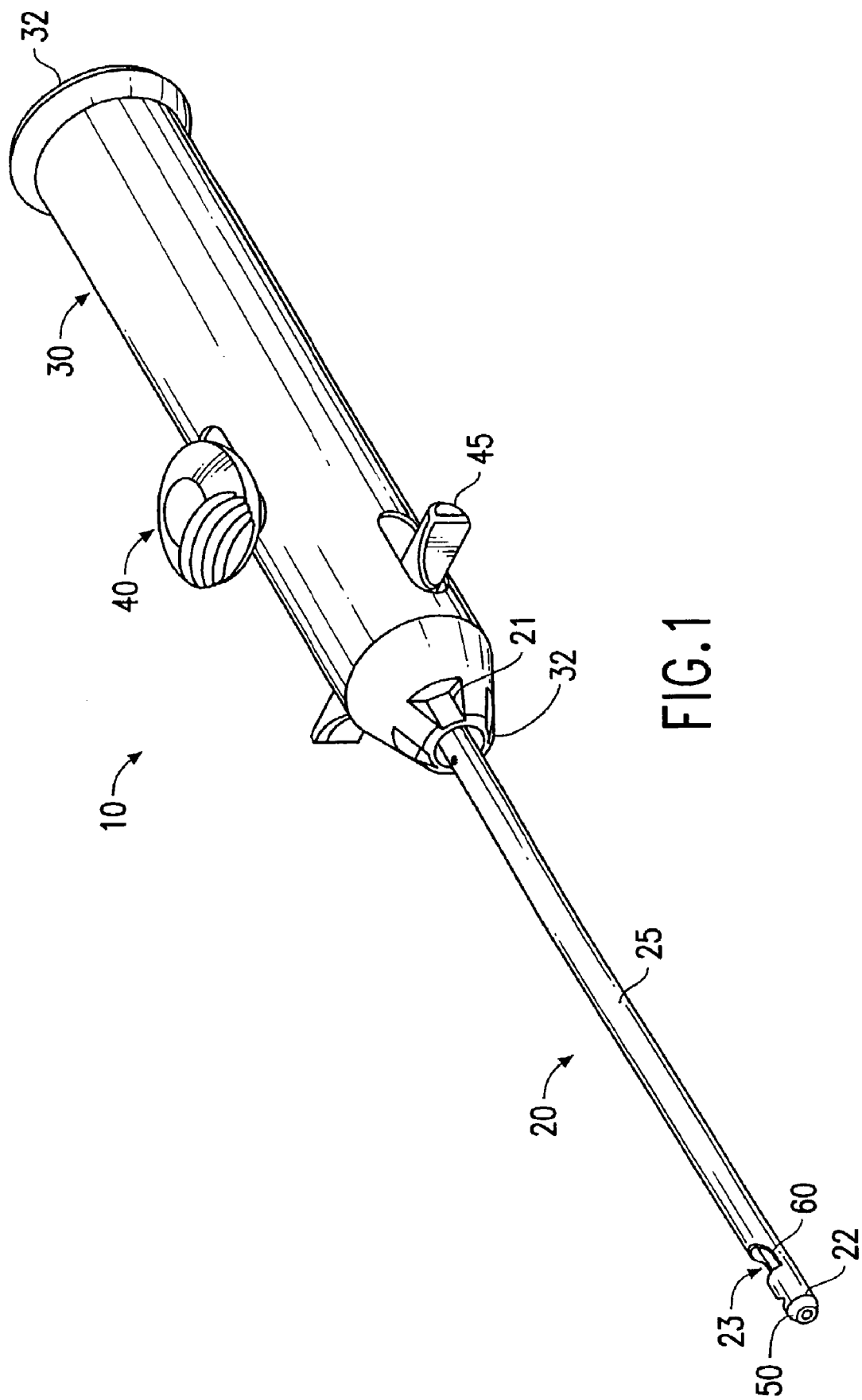
FIG. 1 is a isometric view of an exemplary embodiment of a suture trimmer in accordance with the present invention.

Referring now to FIG. 1 there is shown an exemplary embodiment of a suture trimmer in accordance with the present invention. The suture trimmer comprises a shaft assembly having a proximal end and distal end, a handle disposed at the proximal end of the shaft, and a first and second lever extending from the handle, wherein the first lever and second lever are operatively associated with a cutting member and a suture retaining device respectively.

As shown in FIG. 1, the suture trimmer includes a shaft assembly 20. The shaft assembly 20 includes an elongated member 25 having a proximal end 21 and a distal end 22. An opening 23 is formed in the elongated member 25 adjacent to the distal end 22. A fitting 50 may be disposed adjacent to the distal end 22 of the shaft assembly 20. The fitting 50 may have a cross-sectional size no greater than that of the elongated member 25. The fitting 50 further includes a groove formed therein, wherein the groove is adapted to receive at least one length of suture therethrough. In a preferred embodiment, the groove is configured to receive at least two sutures therethrough. The distal face of the fitting 50 is configured to engage a knot formed in a suture loop, thereby enabling the suture trimmer 10 to be utilized as a knot pusher and advance the knot to an incision site. The face of the fitting may be formed having a convex, concave, or flat surface. Alternatively, the face may be formed at an angle relative to an axis extending through the shaft assembly.

The fitting may be retained within the bore of the elongated member through the use of mechanical fasteners or suitable adhesives. It is further contemplated that the fitting may be formed onto the elongated member utilizing a molding process. Alternatively, the fitting and elongated member may be integrally formed. The fitting is preferably fabricated of a bio-compatible material, such as metal or plastic.

The shaft assembly 20 further comprises a cutting member 60 and a suture retaining member 28 disposed within the bore of the elongated member. The cutting member 60 and the suture retaining member 28 may be retained within the bore of the elongated member coaxially, though it is contemplated that they may be retained in other manners, such as, side-by-side or offset. Both the cutting member 60 and the suture retaining member 28 are disposed for movement within the bore of the elongated member. In various embodiments, cutting member 60 is slidably or rotatably disposed within elongated member (i.e. shaft) 25, and suture retaining member 28 is either slidably or rotatable disposed within elongated member (i.e. shaft) 25.

Figure 2:
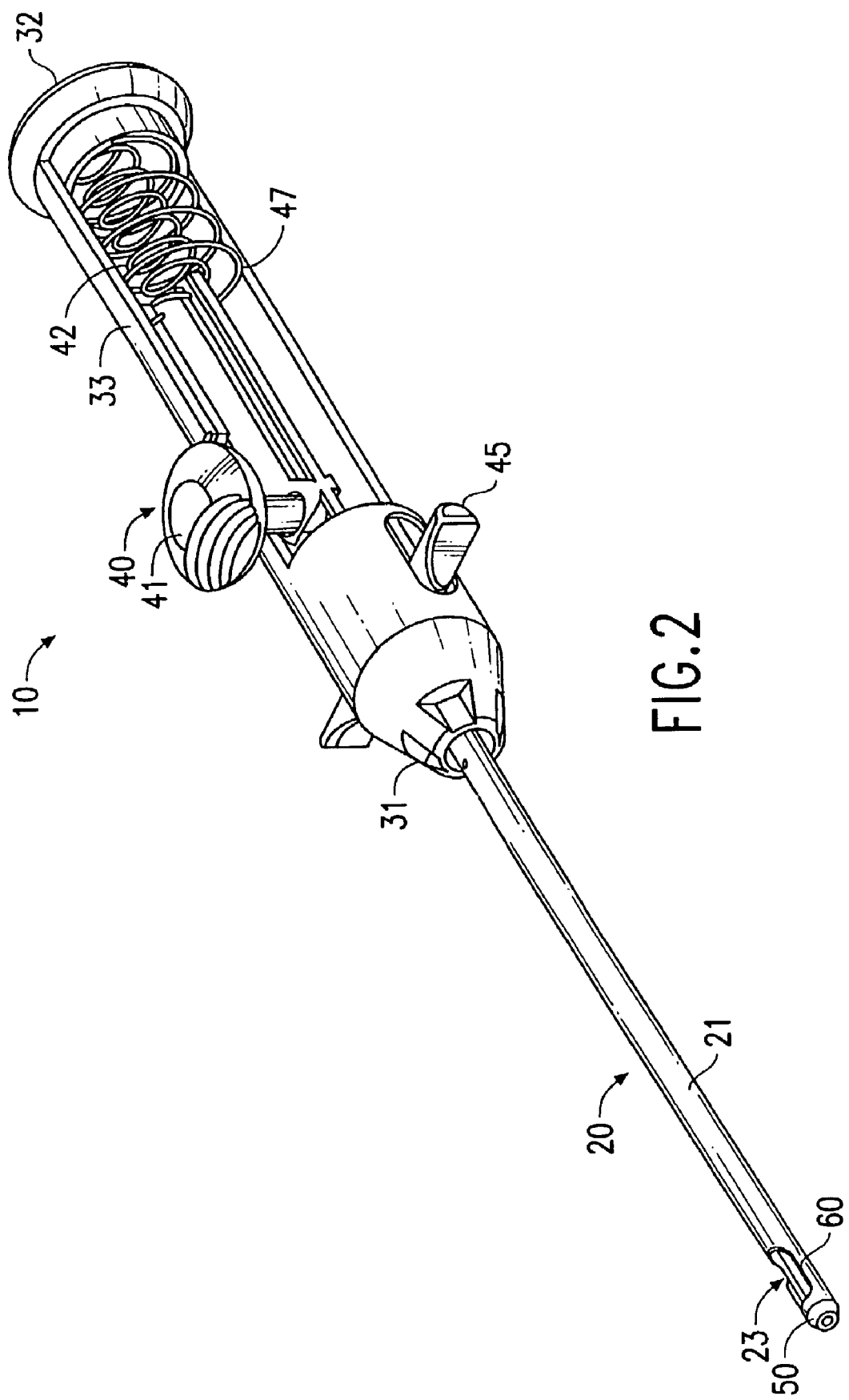
FIG. 2 is a partial cut-away isometric view of the suture trimmer in accordance with the present invention.

Preferably, the handle of the device includes two levers with the first lever being operatively coupled to the suture retainer and the second lever being operatively coupled to the cutting member. For example, as shown in FIG. 1, a first lever 40 is coupled to suture retainer 28. Lever 40 is preferably biased so that when an operator pulls back on lever 40, suture retainer 28 is moved in a proximal direction. A second lever 45 is coupled to the cutting member 60 adjacent to the proximal end. The lever 45 is further configured to engage a biasing member 42 as shown in FIG. 2.

Figure 3:
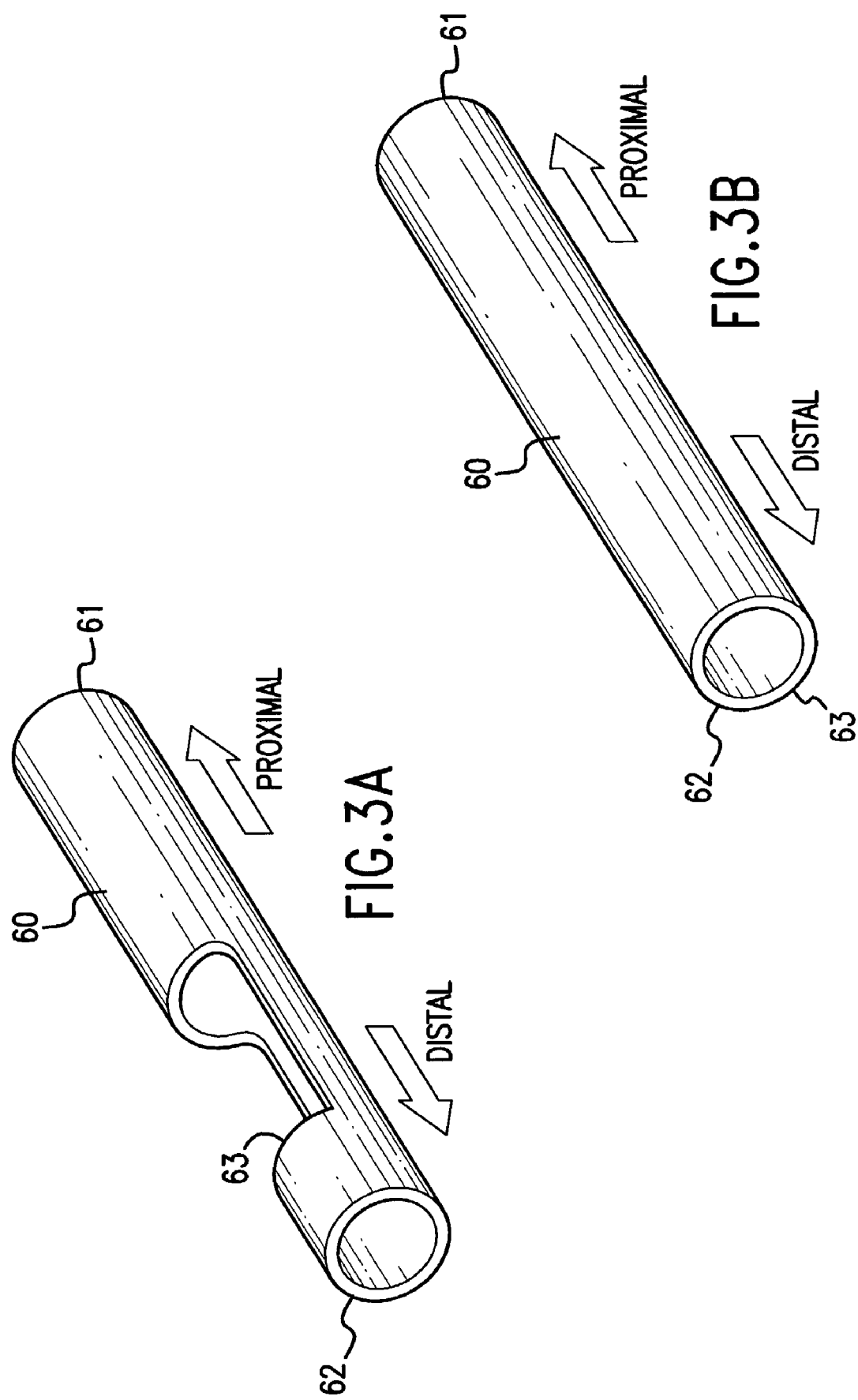
FIG. 3A is a partial perspective view of a first embodiment of the cutting member in accordance with the present invention.
FIG. 3B is a partial perspective view of a second embodiment of the cutting member in accordance with the present invention.

As shown in FIGS. 3A and 3B, various exemplary embodiments of cutting member 60 are provided. For example, cutting member 60 may comprise an elongated member having a proximal end 61 and a distal end 62. A cutting edge 63 is formed within the cutting member 60 adjacent to the distal end 62. As shown in FIG. 3A, a sharpened cutting edge 63 may be formed to cut suture when cutting member 60 is moved in a proximal direction. Conversely, as shown in FIG. 3B, the distal end 62 of cutting member 60 may be sharpened to act as the cutting edge 63, thus cutting suture when cutting member 60 is moved in a distal direction. Thus, as will be further explained, FIG. 3A illustrates a "pull-to-cut" embodiment of the cutting member of the present invention, whereas FIG. 3B illustrates a "push-to-cut" embodiment of the cutting member of the present invention.

The cutting member 60 may be constructed of a bio-compatible material that is capable of having a sufficiently sharp cutting edge 63 formed therein. For example, surgical stainless steel may be utilized as well as titanium. Furthermore, it is contemplated that the cutting member may comprise one or more elements coupled together. For example the shaft of the cutting member may be constructed of a bio-compatible material such as plastic and the cutting edge 63 may be formed of metal wherein the two pieces are combined to form a single element.

Figure 4:
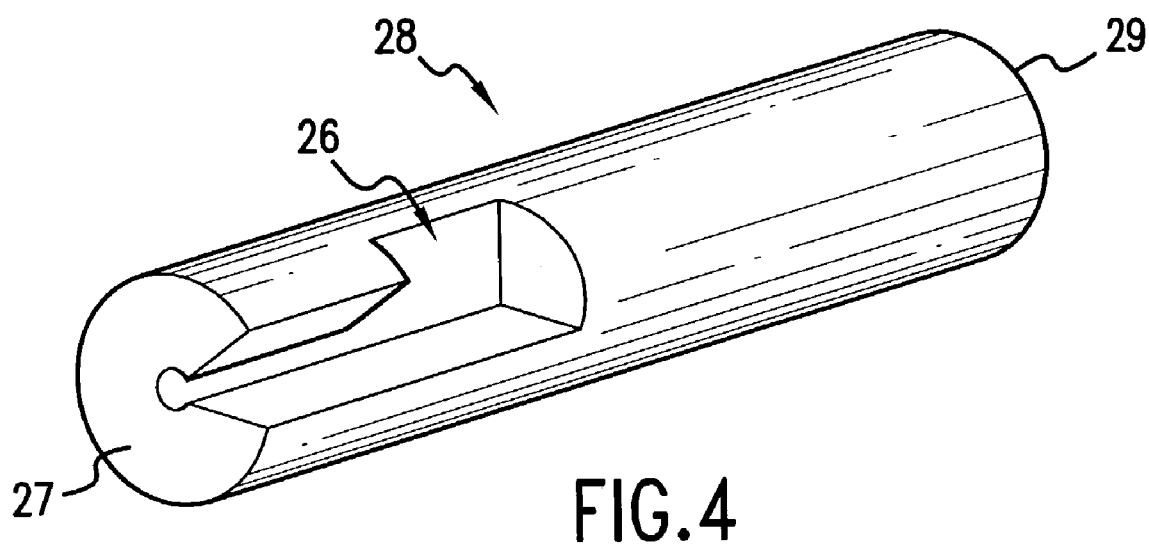
FIG. 4 is a partial perspective view of a first embodiment of the suture retainer in accordance with the present invention.

Referring now to FIG. 4, there is shown the suture retainer in accordance with the present invention. As shown in FIG. 4, the suture retainer 28 includes a proximal end 29, a distal end 27, and a suture protector 26. In preferred embodiments, suture protector 26 comprises a groove in suture retainer 28 through which a suture can pass when the suture has entered the device. Thus, the suture passes through groove 26 and exits out of the distal end 27 of suture retainer 28. Lever 40 is connected to the proximal end 29 of the suture retainer 28. This lever is configured to be slidably received within the handle 33 as shown in FIG. 2. The lever 40 is further configured to receive a biasing member 47, wherein the biasing member retains suture retainer 28 in a position wherein the suture retainer projects into the opening 23 formed in the elongated member of the shaft assembly 20.

The suture retainer may be constructed of a bio-compatible material such as metal or plastic. In a preferred embodiment the suture retainer is constructed of a bio-compatible plastic. Additionally, the suture retainer may be constructed of multiple pieces, wherein the suture retainer and lever are assembled utilizing known methods of mechanical fastening or through the use of an adhesive. It is further contemplated that the suture retainer and lever may be integrally formed, such as through the use of injection molding.

Figure 5:
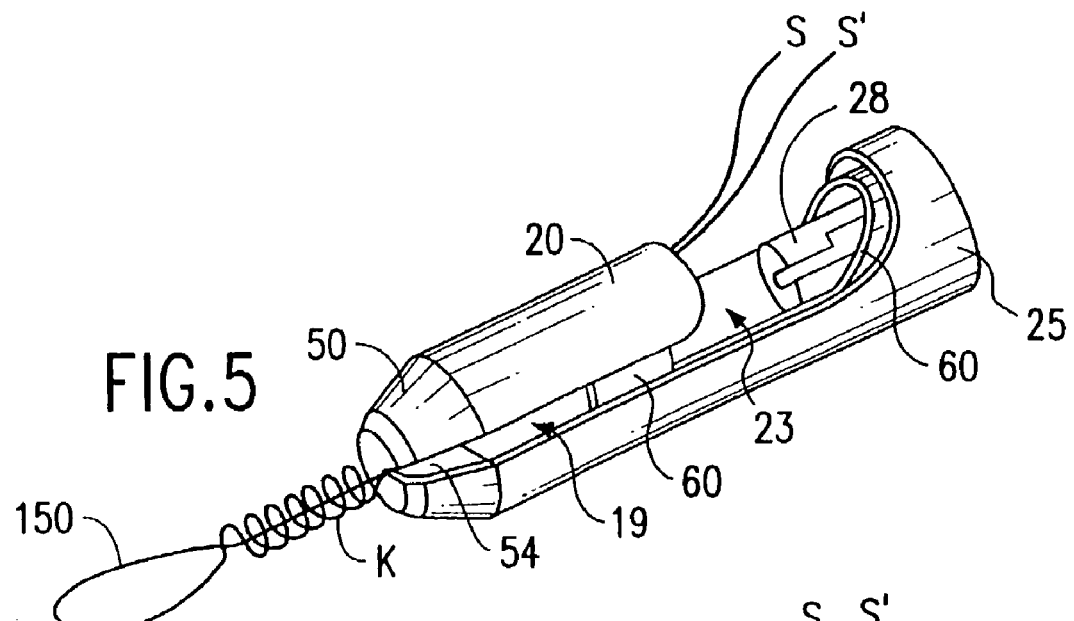
FIG. 5 is a partial isometric view of the distal tip of the suture trimmer in accordance with the present invention illustrating a suture loop disposed therethrough and the suture retainer is in a retracted position.
Figure 6:
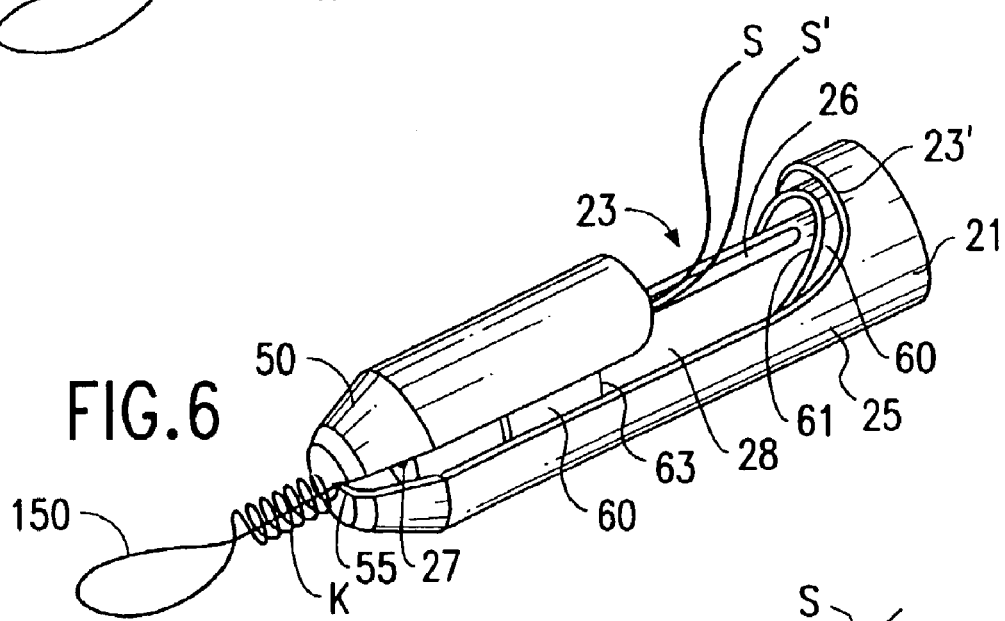
FIG. 6 is a partial isometric view of the distal tip of the suture trimmer in accordance with the present invention illustrating a suture loop being disposed therethrough wherein the suture retainer is in a deployed (i.e.: distally advanced) position.
Figure 7:
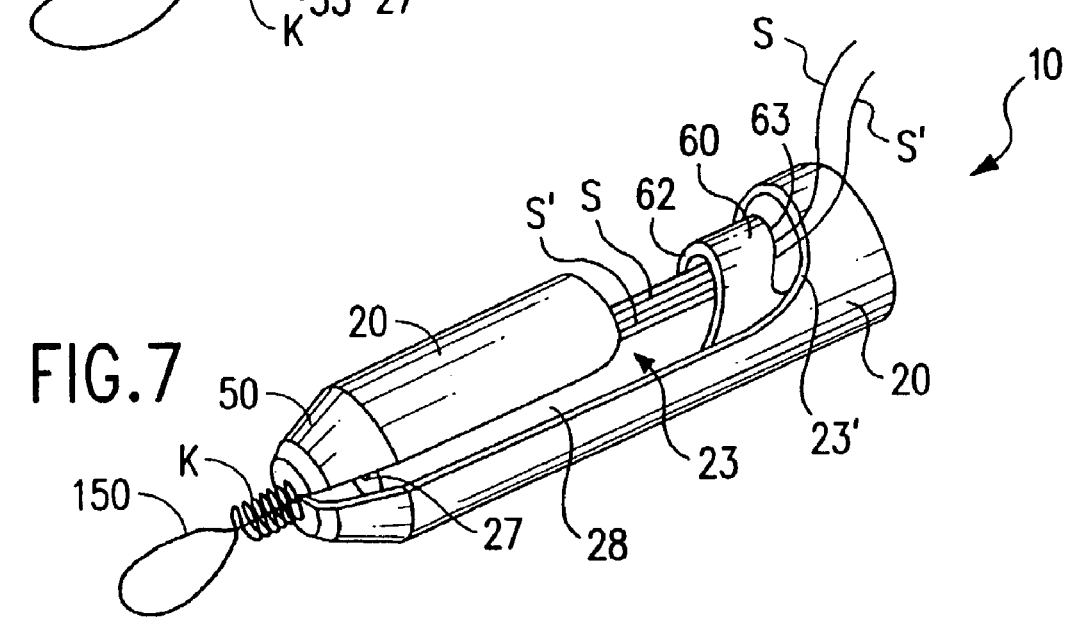
FIG. 7 is a partial isometric view of the distal tip of the suture trimmer in accordance with the present invention illustrating a suture loop being disposed therethrough wherein the cutting member as shown in FIGS. 3A and 5 has been moved proximally to sever the suture.

Referring now to FIGS. 5 to 7 there is shown the distal end portion of the suture trimmer 10 in accordance with the present invention in use. As shown, a suture loop 150 has been formed utilizing a length of suture, wherein the suture loop includes a knot K and two free ends, S and S', of suture extending therefrom.

As illustrated in FIG. 5, the suture retainer 28 has been withdrawn (i.e.: moved proximally) into the bore of the shaft assembly 20 thereby allowing at least one free end of suture S to be disposed through the groove 54 formed in the fitting and groove 19 formed in the wall of the elongated member 25 and to extend out the opening 23 formed in the side of the elongated member 25.

Referring now to FIG. 6, there is shown the distal tip of the suture trimmer in accordance with the present invention wherein the suture retainer 28 has been released, thus allowing the biasing force to move suture retainer 28 in a distal direction within elongated member 25. Specifically, the biasing member is coupled to the proximal end of the suture retainer, causing the suture retainer to advance distally and be received within the bore of the distal end of the shaft assembly. As shown the suture protector 26 (e.g.: groove) shields the suture S, S' from the edge of the opening 23 formed in the elongated member 25. The suture protector 26 ensures that the free end of the suture S cannot contact the edge of the opening 23 formed in the elongated member 25 which may be sharp. If the suture were allowed to contact the edge of the opening, a nick or cut may be formed in the suture, this may lead to failure of the suture before the knot can be advanced and tightened by applying a force to the free end of the suture. If the suture were to fail the surgeon would be required to place a second suture loop adjacent to the first suture loop and repeat the process of advancing and tightening the knot.

Referring now to FIG. 7, (which shows the embodiment of cutting member 60 as illustrated in FIG. 3A) there is shown a partial view of the distal tip of the suture trimmer 10 in accordance with the present invention wherein the cutting member 60 has been actuated to cut the sutures after the suture loop has been tightened. Upon actuation, the cutting edge 63 moves in a proximal direction from a shielded position within the distal tip portion of the shaft assembly 20. Specifically, cutting member 60 is moved proximally from the shielded position by applying a force to the lever 45 (FIG. 1), the lever 45 being coupled to the proximal end of the cutting member 10. As described above, the cutting member 60 is actuated by pulling back on the lever 45, thereby advancing the lever towards the proximal end of the suture trimmer 10 and compressing a second biasing member disposed within the handle. The cutting member 60 includes a sharpened cutting edge 63. It is further contemplated that the proximal edge 23' of the opening 23 may also be sharpened to assist in cutting the suture between cutting edge 63 and proximal edge 23'. As described above and illustrated in FIG. 7, the cutting member 60 of the suture trimmer 10 moves relative to the elongated member 25 of the shaft assembly 20.

FIGS. 5 to 7 as described above incorporate the embodiment of the cutting member 60 as shown in FIG. 3A. In this embodiment, the suture is preferably cut in a "pull-to-cut" approach in which the cutting member moves in a proximal direction to cut the suture. Alternatively, the present invention may instead incorporate the embodiment of the cutting member 60 as shown in FIG. 3B in a "push-to-cut" approach. In such a "push-to-cut" approach, the cutting member is advanced distally, with the suture being cut by the distal end of the cutting member. Further examples of "push-to-cut" approaches are discussed in the various embodiments which follow herein.

Figure 8:
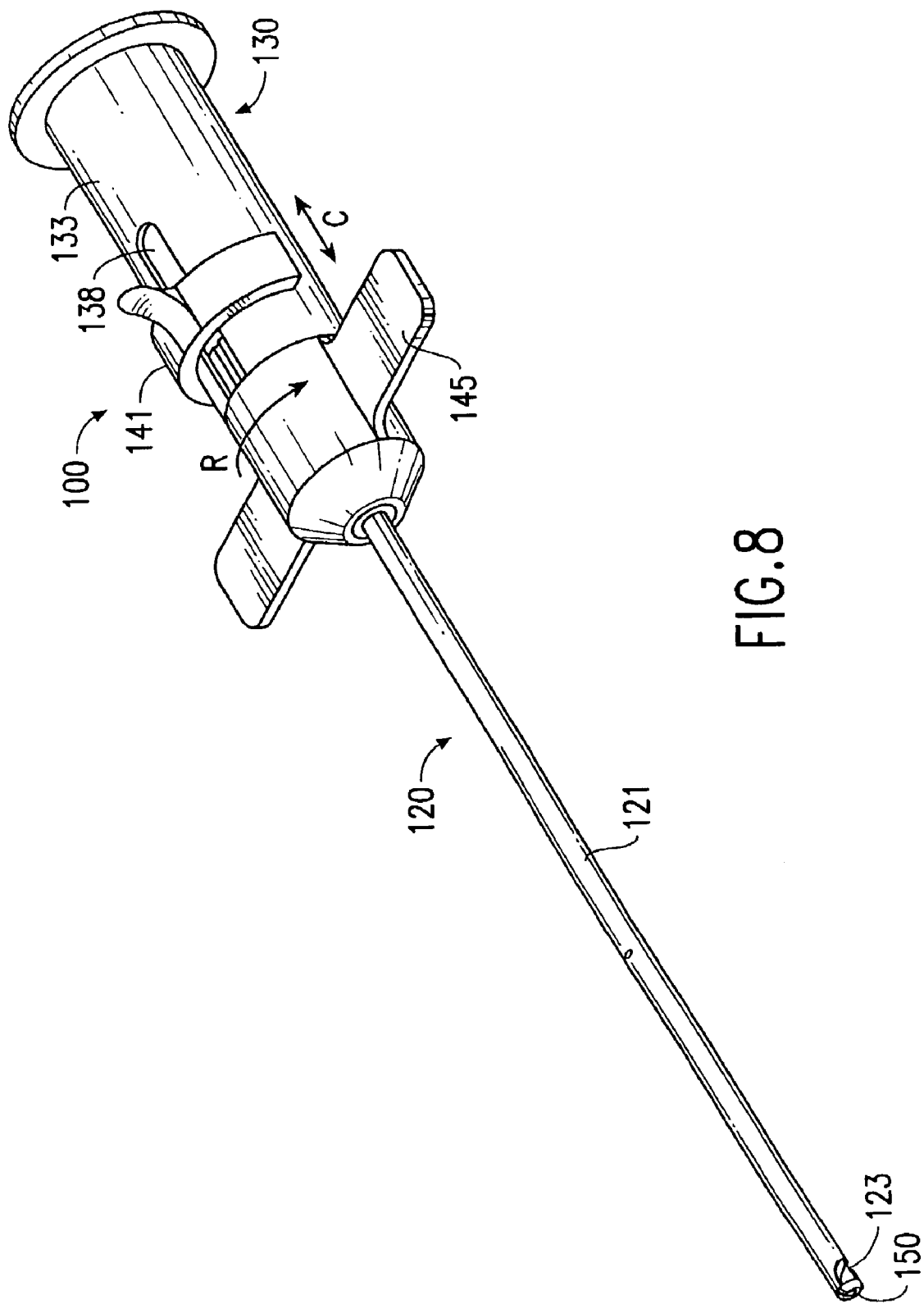
FIG. 8 is an isometric view of an alternative embodiment of a suture trimmer in accordance with the present invention.

Referring now to FIG. 8 there is shown an alternative embodiment of a suture trimmer 100 in accordance with the present invention. As shown in FIG. 8, the suture trimmer 100 comprises a handle 130, an elongated shaft assembly 120, a distal tip fitting 150, a first lever 145 and a second lever 141. As shown in FIG. 8, the first lever 145 is configured to rotate R about the handle 130 in addition to being configured to be translated along an axis extending through the handle 130. The second lever 141 is configured to translate along an axis extending through the handle 130. The functionality of the first and second levers will be described in greater detail below with reference to FIG. 9. It is further contemplated that the first lever 145 may be embodied having a generally cylindrical shape and being disposed about the distal end of the handle. For example, the first lever 145 may be a ring.

Figure 9:
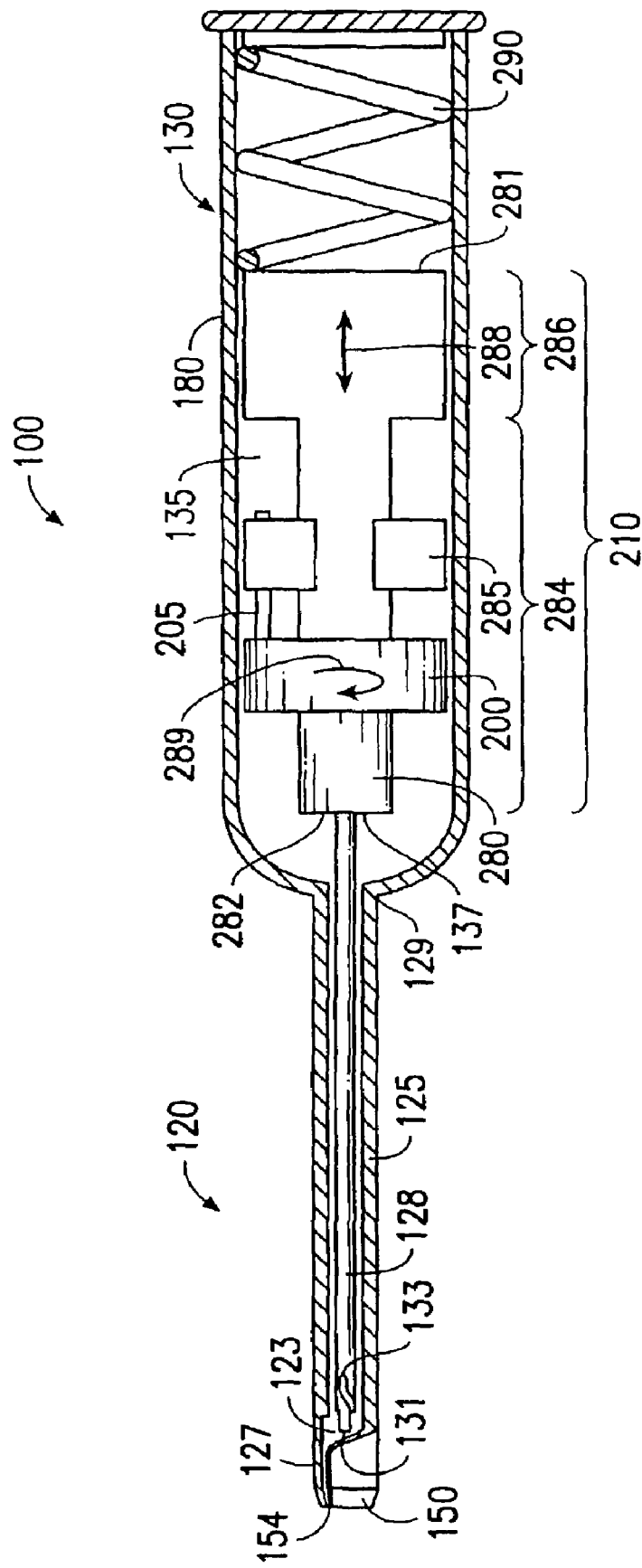
FIG. 9 is a cross-sectional view of the suture trimmer in accordance with FIG. 8 illustrating the slider assembly disposed within the handle.

Referring now to FIG. 9, there is shown the elongated shaft assembly 120 of the suture trimmer 100. As shown the elongated shaft assembly 120 comprises a hollow elongated member 125 having a proximal end 129 and a distal end 127. An opening 123 is formed in the wall of the elongated member 125 adjacent to the distal end 127 thereof. The opening 123 is further configured to include a sharpened cutting edge, which is formed on the proximal end of the opening 123. The elongated member 125 may be constructed of a bio-compatible metal such as stainless steel, titanium or a bio-compatible coated material. Alternatively, the elongated member may be constructed of a bio-compatible plastic. The elongated member in a preferred embodiment has a circular cross-sectional profile, though it is contemplated that the elongated member may be constructed having other cross-sectional profiles such as square, triangular, or oval.

A suture retaining member 128 is disposed within the bore of the elongated member 125. The suture retaining member 128 includes an elongated member having a proximal end 137 and a distal end 131. A suture receiving groove 133 is formed in the distal end of suture retaining member 128. The suture retaining member 128 is slidably and rotatably disposed within the bore of the elongated member 125. The suture retaining member 128 may be coaxially disposed within the bore of the elongated member 125, or arranged in an offset manner. The proximal end of the suture retaining member is coupled to the first and second levers of the suture trimming device, the function of which will be described in detail below.

The shaft assembly 120 may further include a fitting 150 disposed adjacent to the distal end 127 of the shaft assembly 120. The fitting 150 has a cross-sectional size no greater than that of the elongated member 125. The fitting 150 further includes a groove 154 formed therein, wherein the groove 154 is configured to receive at least one length of suture therethrough. In a preferred embodiment, the groove 154 is configured to receive at least two sutures therethrough. The distal face of the fitting 150 is configured to engage a knot formed in a suture loop, thereby enabling the suture trimmer 100 to be utilized as a knot positioner and advance the knot to an incision site. The face of the fitting may be formed having a convex, concave, or flat surface. Alternatively, the face may be formed at an angle relative to an axis extending through the shaft assembly.

As shown in FIG. 9, the proximal end 129 of the shaft assembly 120 is connected to a handle 130. Handle 130 comprises a generally cylindrical casing 180 having an open interior chamber 135 and an axial slot 138 (as shown in FIG. 8). A slider assembly 210 is reciprocatably disposed within the chamber 135, the slider assembly having a proximal end 281 and a distal end 282, the distal end 282 coupled to the proximal end 137 of the suture retainer 128. The slider assembly further includes a first lever 145 and a second lever 141 coupled to the slider assembly 210 as shown in FIG. 8. A biasing member 290 is further disposed within the chamber 135 wherein the biasing member 290 is disposed in a space proximal the proximal end of the slider. The biasing member applies a force to the slider assembly so that suture retainer 128 will remain in a distally advanced position. It is further contemplated that the suture trimmer 100 may include more than one biasing member. For example, two biasing members may be provided in combination and configured to provide a progressive spring rate.

The handle, slider assembly, and levers may be manufactured of materials such as metals or plastics. In a preferred embodiment, the handle and levers are manufactured of plastic utilizing an injection molding process.

As shown in FIG. 9 the slider assembly 210 is constructed of a first member 280 having a proximal end 281, a distal end 282, a reduced diameter portion 284 and an enlarged diameter portion 286 disposed therebetween. The first member 280 further includes a plurality of members 285 disposed radially about a reduced diameter portion 284 of the first member 280. A rotating ring 200 is rotatably disposed about the reduced diameter portion 284. The rotating ring further includes an engaging member 205, wherein the engaging member is configured to engage one of the plurality of members 285 extending radially about the reduced diameter portion.

The proximal end 281 is further configured to receive a basing means 290. The biasing means may comprise a spring, elastic foam or devices that have similar mechanical properties.

The slider assembly and the suture retainer may be constructed as a unitary member or alternatively may be constructed of multiple pieces which are then assembled using known manufacturing methods.

Referring now back to FIG. 8, the first lever 145 is coupled to the rotating ring 200, wherein a pin (not shown) is utilized to couple the first lever 145 to the rotating ring 200. By applying a rotational force 289 to the rotating ring causes the engaging member 205 to engage at least one of the plurality of members 285, thereby causing the suture retainer 280 to rotate within the shaft assembly 120. The second lever 141, shown in FIG. 8, is coupled to the increased diameter portion 285 of the slider assembly 210. The second lever 141 may be connected through the use of a pin (not shown) disposed within the increased diameter portion, the pin extending through a groove formed in the handle as shown in FIG. 8. A force may be applied to the second lever, thereby causing the suture retainer 128 and the second lever to be displaced proximally, the suture retainer 128 moving proximally within the elongated member 125 of the shaft assembly 120. When such force is applied, suture retainer 128 will be moved proximally, thus providing an opening for the suture to be received through opening 123 in elongated member 125. Thereafter, the force on the second lever can be released such that suture retainer 128 springs forward in a distal direction, thereby trapping the suture in the device, as explained below.

Referring now to FIGS. 10 to 13, there is shown a partial view of the distal tip of the suture trimmer 100 in accordance with the present invention disposed in various states of use, each of which will be described in detail below with reference to the Figures.

Figure 10:
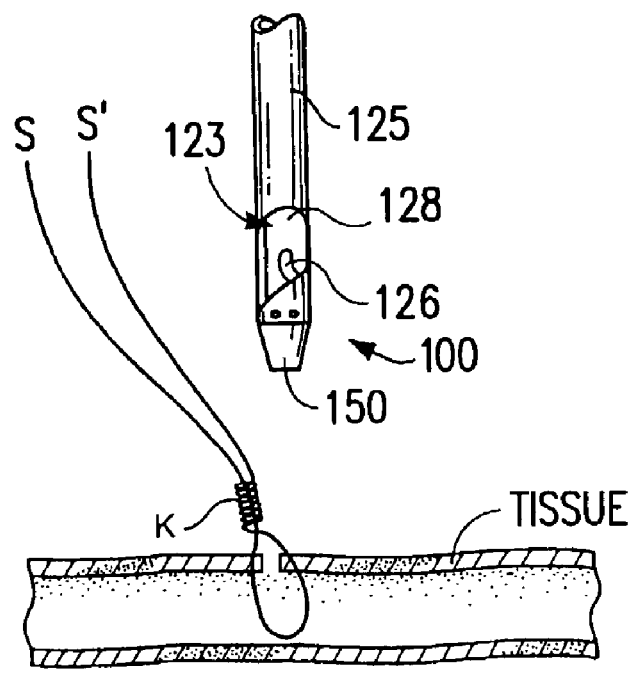
FIG. 10 is a partial view of the distal tip of the suture trimmer in accordance with FIG. 8, wherein a suture loop has been formed in a patient's tissue.

Referring now to FIG. 10, there is shown the distal end of the suture trimmer 100, wherein the suture retaining member 128 is shown disposed in a distally advanced position. A suture loop has been formed in tissue as shown, the suture loop comprises a knot K formed in a loop of suture, wherein the two free ends S and S' of the suture extend from the knot. In an optional preferred method of use, the tissue is a femoral artery and any of the present suture trimmer embodiments may be used to sever the loose ends of a loop of suture which has been used to close a hole in the femoral artery. Such femoral artery closure uses may be preferably conducted in conjunction with agent delivery systems described herein.

Figure 11:
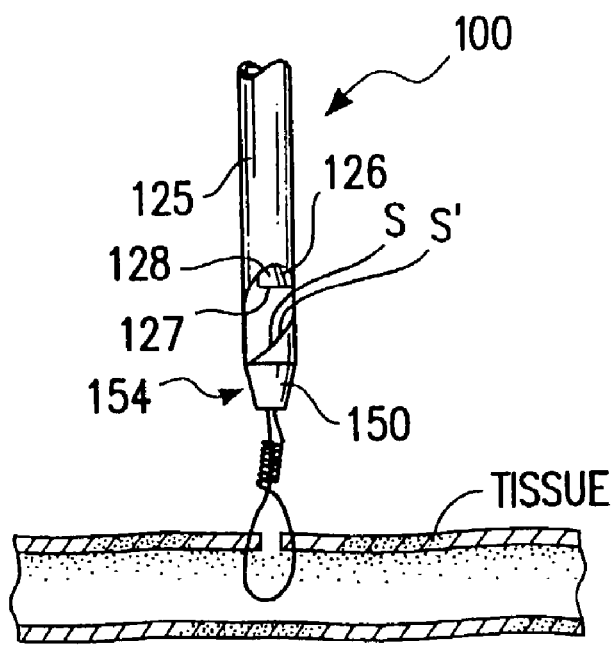
FIG. 11 is a partial view of the distal tip of the suture trimmer of FIG. 8, wherein the suture retainer has been retracted to provide an opening to receive the suture into the device.

Referring now to FIG. 11 there is shown the distal tip, wherein the suture retainer 128 has been retracted (i.e. moved proximally) within the elongated member of the shaft assembly 120 by applying a force to the second lever 141. The two free ends of the suture as disposed through a groove 154 formed in the fitting 150 and distal end of the elongated member 125, the two free ends of suture extend through the opening 123 formed within the elongated member 125.

Figure 12:
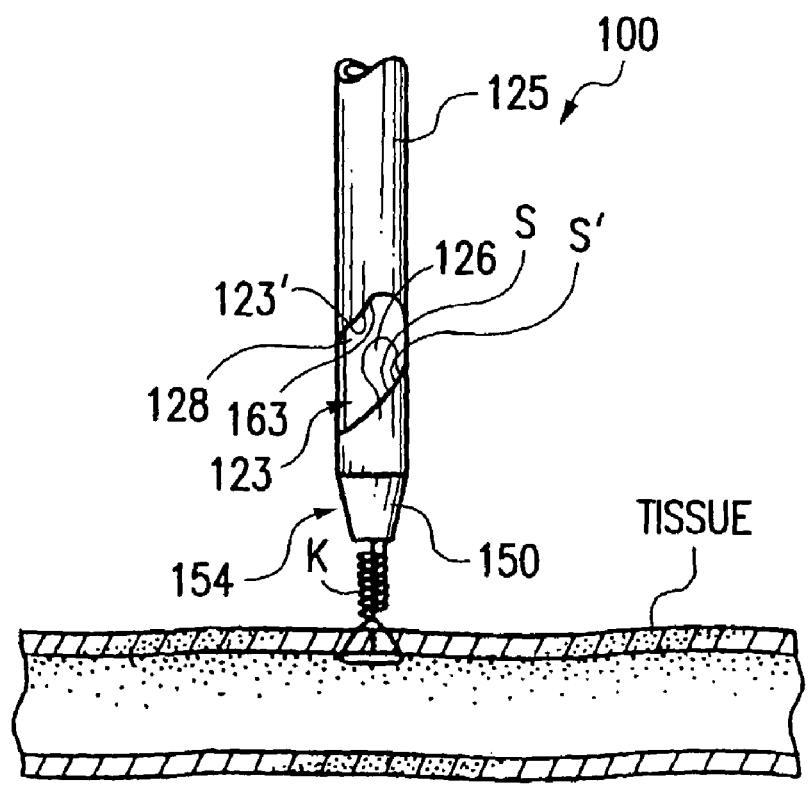
FIG. 12 is a partial view of the distal tip of the suture trimmer of FIG. 8, wherein the suture retainer has been advanced distally and then rotated to align the free ends of the suture with the cutting edge formed in the opening of the shaft of the suture trimmer.

Referring now to FIG. 12, there is shown the distal tip of the suture trimmer 100 wherein the force applied to the second lever 141 (FIG. 8) has been released, thereby allowing the suture retaining member 128 to advance distally within the bore of the elongated member 125. Optionally, a rotational force may be applied to the first lever 145 (FIG. 8), thereby causing the suture retaining member to rotate within the bore of the shaft assembly. By rotating the suture retaining member 128, the groove 154 may be effectively closed, thus retaining the two free ends of the suture within the distal tip of the suture trimmer 100. As can be seen in FIG. 12, the groove 126 in suture retainer 128 can be used to align the two free ends of suture S and S' with a sharpened cutting edge 163 formed in the proximal end 123' of opening 123. Furthermore, optional rotation of the suture retaining member 128 can further align the two free ends of the suture with the sharpened cutting edge 163 formed in the proximal end 123' of the opening 123. Additionally, as shown, the distal end of fitting 150 can be utilized to advance the knot K onto the tissue, such that the knot K can be tightened by pulling up on one of the free ends of the suture S/S'.

Figure 13:
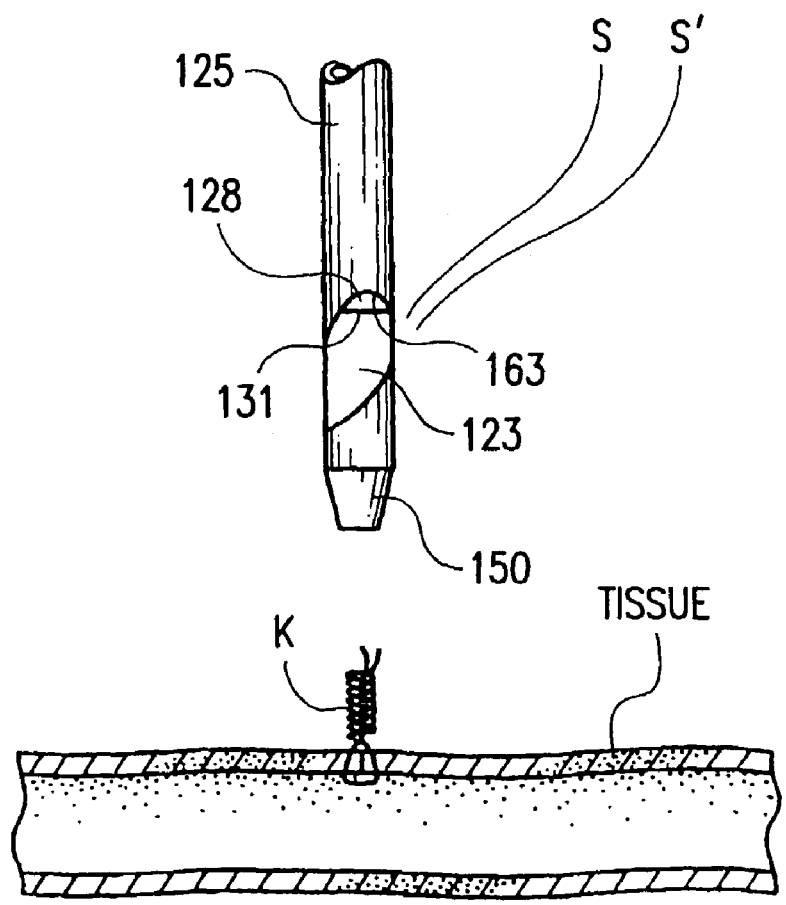
FIG. 13 is a partial view of the distal tip of the suture trimmer of FIG. 8, wherein the suture retainer has been retracted to cut the suture against the cutting edge formed in the opening in the side of the shaft.

Referring now to FIG. 13, there is shown the suture loop after an axial force has been applied to the first lever 145 thereby moving the suture retaining member 128 proximally within the bore of the elongated member thereby advancing the two free ends of the suture into contact with the sharpened cutting edge 163 formed in the opening 123, such that the sharpened cutting edge 163 severs the free ends of the suture adjacent to the knot K as shown.

As described above with reference to FIGS. 8 to 13, it shall be understood that the cutting member of the suture trimmer 100 remains stationary in use. Specifically, the elongated member 125 itself acts as the cutting member in this embodiment of the invention. As shown in FIGS. 10 to 13, a piece of suture to be severed is brought to the cutting edge 163 formed in an edge of opening 123. The suture is severed due to the interference between the suture, the opening 126 formed in the suture retaining member 128 and the cutting edge 163.

Figure 14:
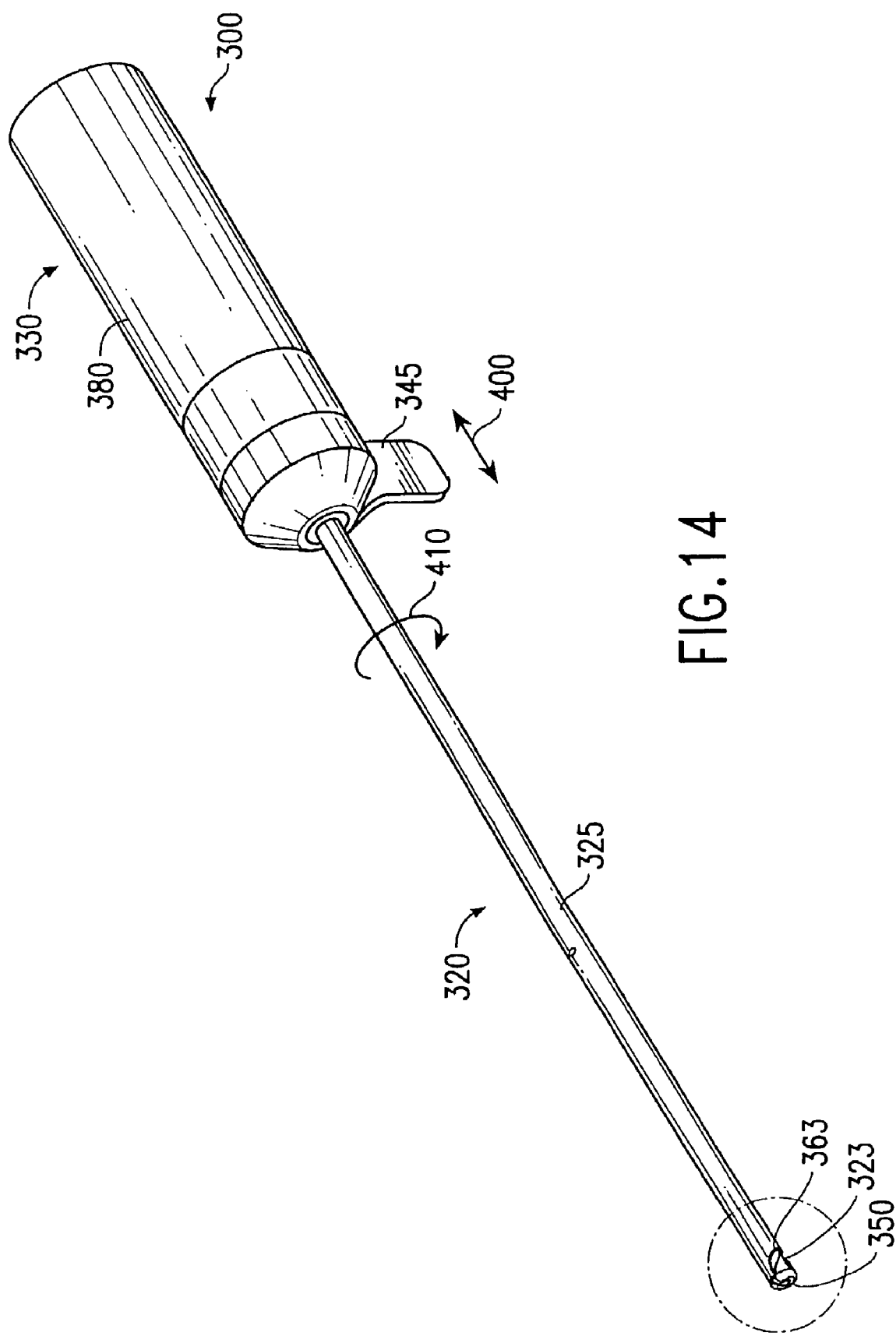
FIG. 14 is perspective view of yet another alternative embodiment of a suture trimmer in accordance with the present invention.

Referring now to FIGS. 14 to 18 there is shown an alternative suture trimmer 300 in accordance with the present invention. As shown in FIG. 14, the suture trimmer 300 comprises a handle portion 330, a shaft assembly 320 and a fitting 350 disposed on the distal end of the shaft assembly. The handle 330, shaft assembly 320 and fitting 350, of the suture trimmer 300 is similar to each of those described above. With regard to FIGS. 15 to 18, there is shown the suture trimmer 300 in accordance with FIG. 14 in use.

Figure 15:
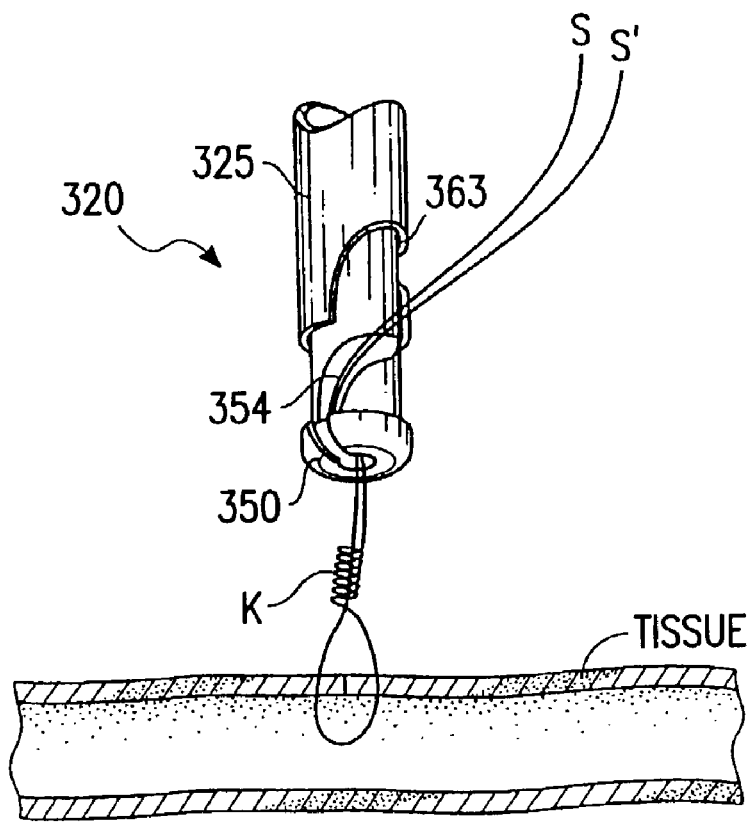
FIG. 15 is a sectional view of the distal tip of the suture trimmer in accordance with FIG. 14 illustrating the elongated member in a proximal (i.e. retracted) position.

Referring now to FIG. 15 there is shown yet another alternative embodiment of a suture trimmer in accordance with the present invention. As shown in FIG. 15, the suture trimmer 300 includes a shaft assembly 320, a fitting 350 disposed on the distal tip of the shaft assembly and lever 345. The suture trimmer 300 includes a retractable, indicated by reference number 400, elongated member 325 connected to lever 345, the lever connected to a handle 380. In addition to being retractable, the elongated member 325 is further configured to rotate, indicated by the reference number 410, about an axis extending between the distal end and proximal end of the suture trimmer 300.

Referring now to FIG. 15, there is shown the distal tip of the suture trimmer 300 wherein the elongated member 325 of the shaft assembly 320 has been retracted, thereby exposing the groove 354 through which the free end(s) of the suture may be disposed as shown.

Figure 16:
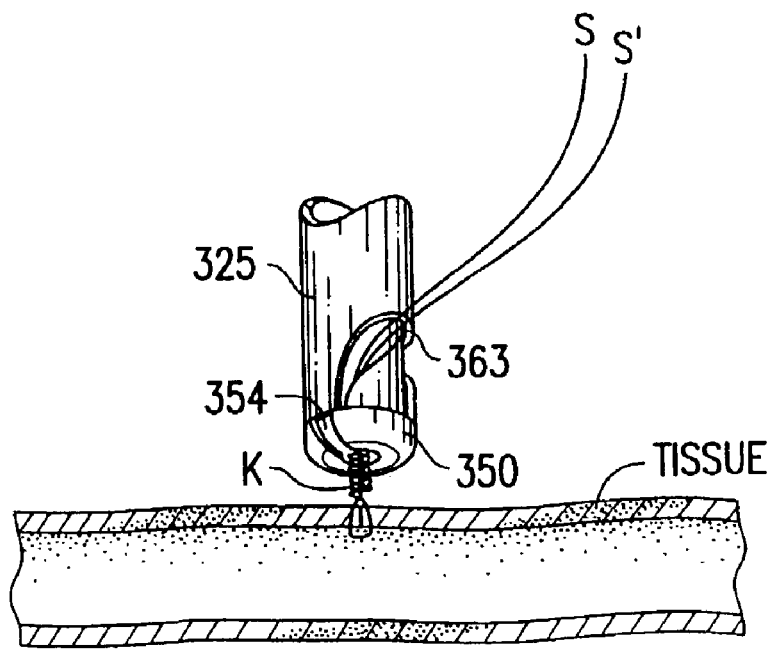
FIG. 16 is a sectional view of the distal tip of the suture trimmer in accordance with FIG. 14, wherein the elongated member has been distally advanced to retain at least one suture in the distal tip of the device.

Referring now to FIG. 16, there is shown the distal tip, wherein the force applied to retract the elongated member 325 has been released, thereby allowing the elongated member 325 to advance as shown. The elongated member 325 is utilized to close the groove 354 when advanced in a distal position as shown in FIG. 16, thereby retaining the free ends of the sutures within the groove 354 as shown. Furthermore, after allowing the elongated member to advance distally as shown, the distal tip of the suture trimmer may be utilized to advance the knot K and substantially close the suture loop.

Figure 17:
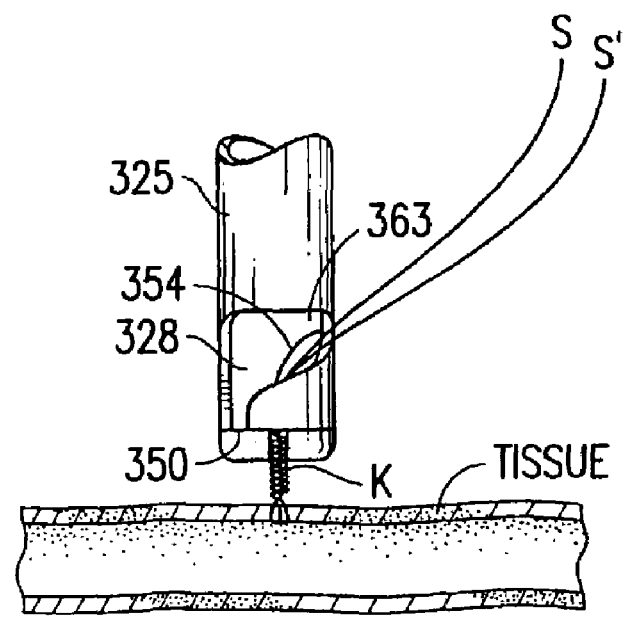
FIG. 17 is a sectional view of the distal tip of the suture trimmer in accordance with FIG. 14, wherein the elongated member of the suture trimmer has been rotated to a cutting position.

Referring now to FIG. 17, there is shown the distal tip of the suture trimmer 300, wherein the elongated member 325 has been rotated counter-clockwise relative to the suture retainer 328. By rotating the elongated member 325 as shown, the free ends of the suture are drawn to a cutting edge 363 formed in the elongated member 325.

Figure 18:
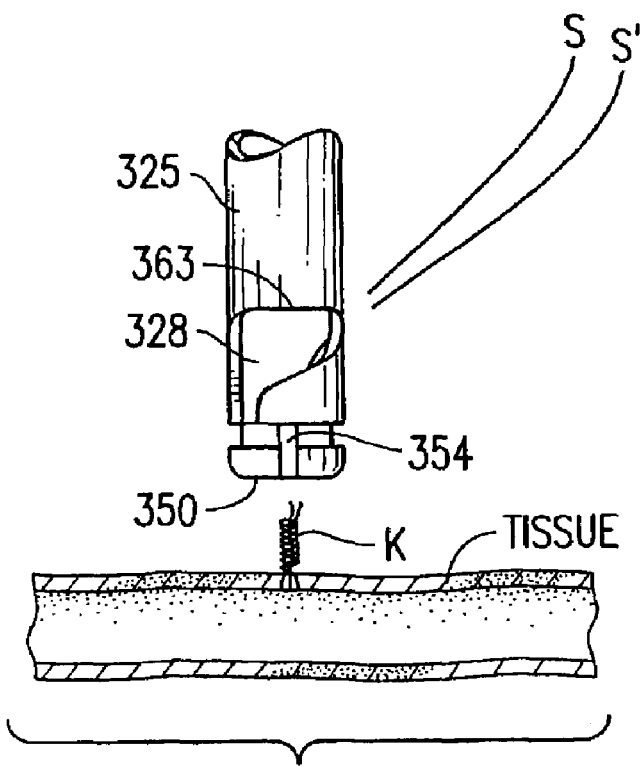
FIG. 18 is a sectional view of the distal tip of the suture trimmer in accordance with FIG. 14, wherein the elongated member has been moved proximally (i.e. retracted) to trim the suture.

Referring now to FIG. 18, there is shown the suture trimmer 300 in accordance with the present invention. As shown in FIG. 18, the elongated member 325 has been retracted relative to the suture retaining member 328. By retracting the elongated member 325, the free ends of the suture are brought into contact with the cutting edge 363 formed within the elongated member 325, thus trimming the free ends of the suture close to the knot K as shown. Although this embodiment of the invention moves the elongated member 325 proximally to sever the tissue, it is be understood that an alternate embodiment may instead move the suture retainer distally to achieve the same result.

Although the suture trimmer 300 is described wherein the elongated body is rotated relative to the suture retaining member 128, it is contemplated that the elongated member may be held stationary and the suture retaining member may be rotated therein. Still further it is contemplated that both the elongated member and the suture retaining member may be rotated respectively.

Still further, it shall be understood that although the embodiments illustrated herein have been described as utilizing levers to advance/actuate/move various features disposed within or upon the suture trimmers it shall be understood that other mechanical devices and assemblies may be utilized to perform the same tasks without departing from the scope of the present invention.

Figure 19B:
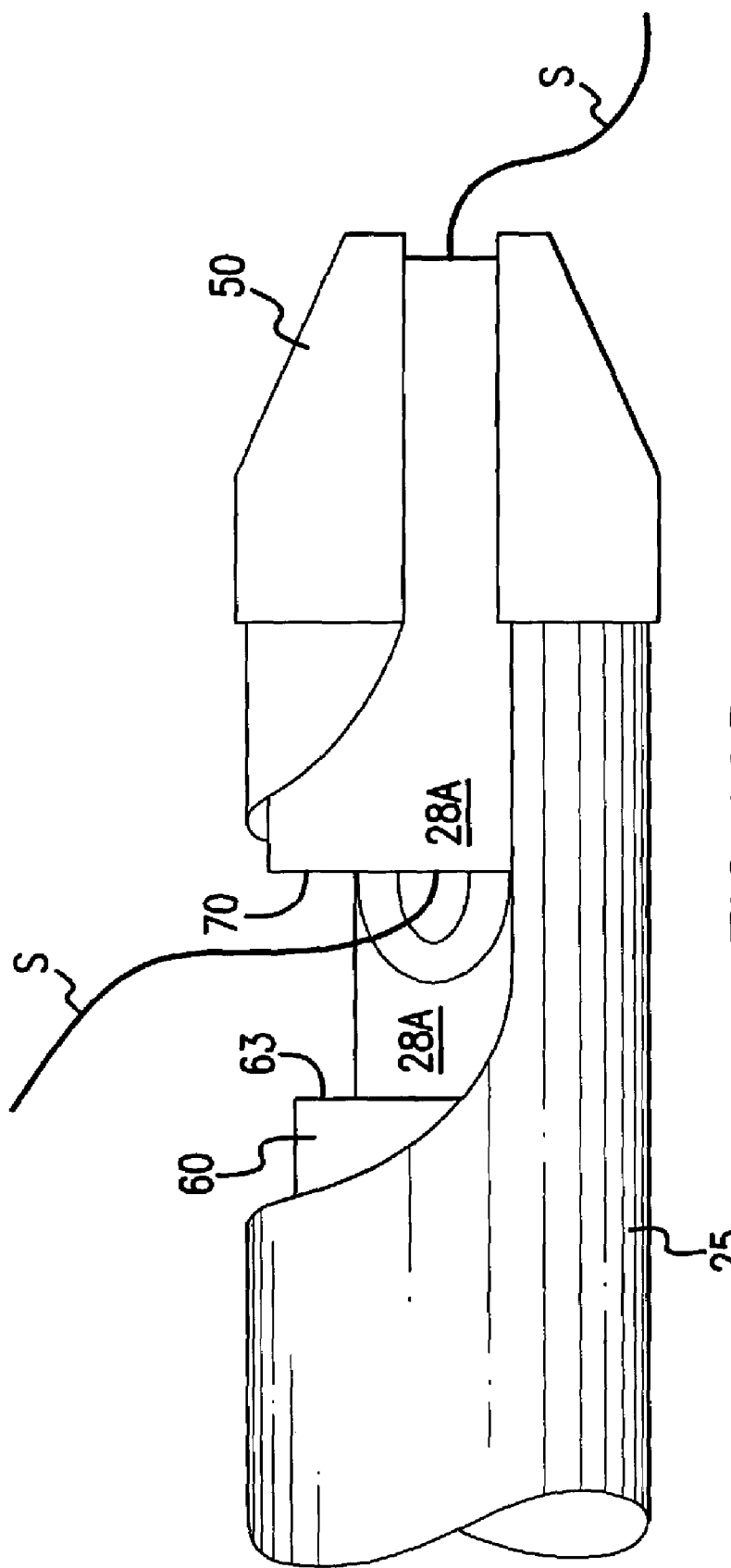
FIG. 19B is a view similar to FIG. 19A, but with the suture retainer rotated to a second position to trap the suture in the device.

In various embodiments of the invention, various suture cutting techniques are employed. For example, as shown in FIGS. 19A to 19C, the suture(s) may be cut between the distal end of the cutting member and an anvil portion of the suture retainer. Alternatively, as shown in FIGS. 20A to 20D, the suture(s) may be cut between the distal end of the cutting member and an anvil portion (such as a proximal edge or surface) of the fitting.

FIGS. 19A to 19C illustrate a "push-to-cut" system in which the cutting member is distally advanced towards a portion of the suture retainer to sever the suture therebetween. In this embodiment, the suture retainer is rotated in one direction to receive the suture therein, and then released so that it rotates in an opposite direction to lock the suture in the device. FIGS. 20A to 20D also illustrate a "push-to-cut" system in which the cutting member is distally advanced towards a portion of the suture retainer to sever the suture therebetween. However, in this embodiment, the suture retainer is moved proximally so that the suture can be positioned within the device. The suture retainer is then released so that is allowed to distally advance to lock the suture therein.

Turning first to FIGS. 19A to 19C, an elongated member (e.g.: a hollow shaft) 25 is provided with a tubular cutting member 60 received therein. A suture retainer 28A is received within the bore of tubular cutting member 60, as shown. Suture retainer 28A is rotatable around central longitudinal axis A. Suture retainer 28A comprises a groove 26A passing therethrough. When suture retainer 28A is rotated to the first position as shown in FIG. 19A, groove 26A is positioned in alignment with both groove 54 in fitting 50 and with opening 23 in elongated member 25. A suture S is received therein as shown. (For clarity of illustration, only a single suture is shown. It is to be understood that a typical use of the present invention will instead have a pair or loop of suture passing therethrough.) After suture S is received in groove 26A, suture retainer 28A is then rotated to the second position as shown in FIG. 19B, thereby locking the suture within the device. Thereafter, as shown in FIGS. 19C and 19D, cutting member 60 is distally advanced to sever the suture between an anvil portion 70 of suture retainer 28A. In exemplary embodiments, anvil portion 70 comprises a flat face of suture retainer 28A which is disposed perpendicular to the axis of the shaft.

Figure 20B:
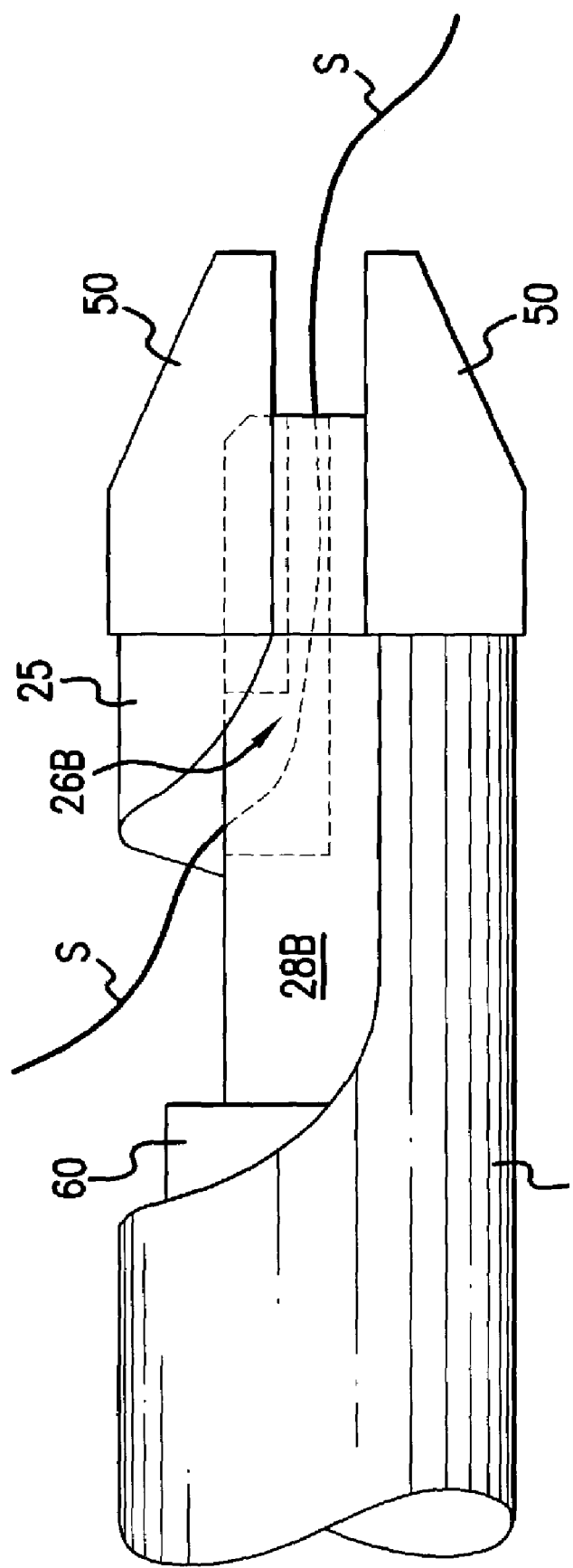
FIG. 20B is a view similar to FIG. 20A, but with the suture retainer moved distally (i.e. advanced) to trap the suture in the device.
Figure 20D:
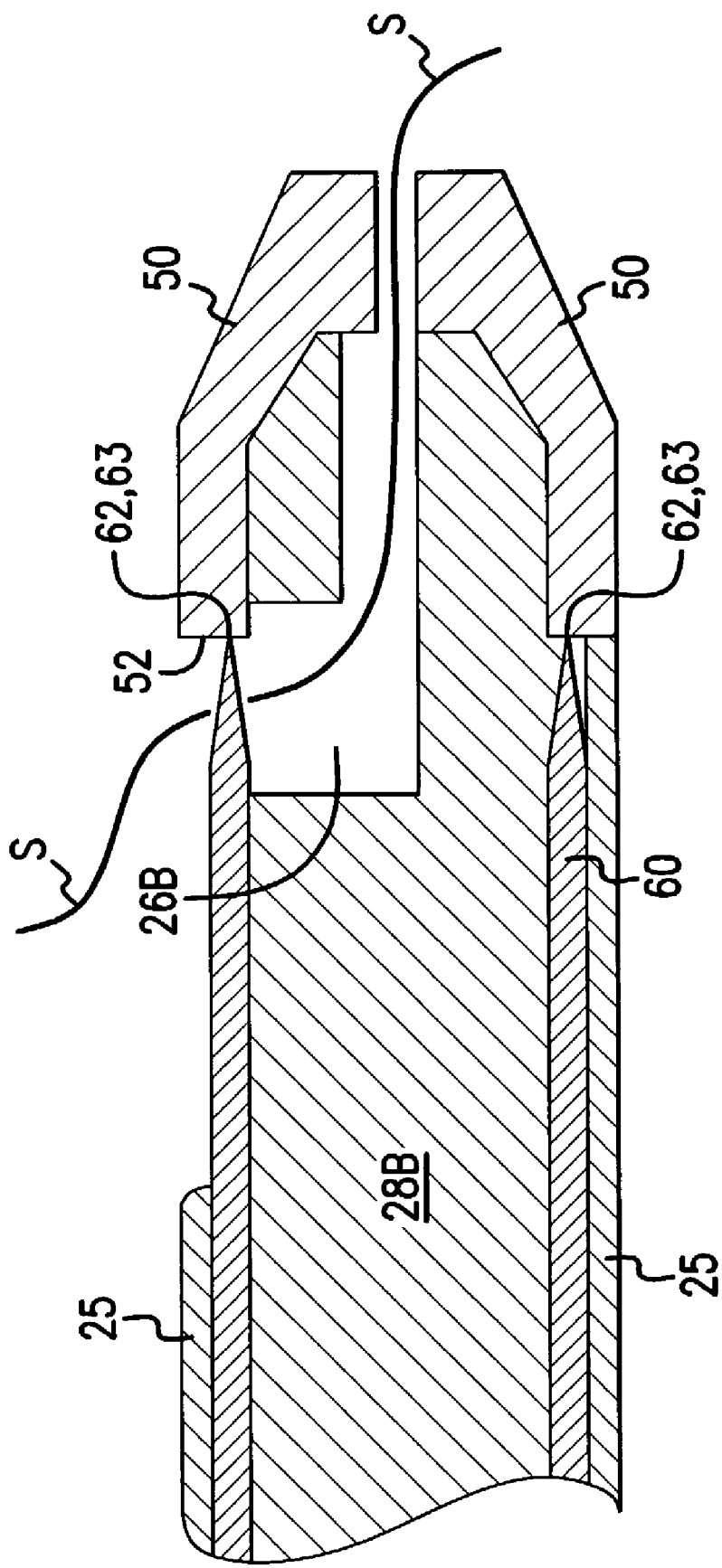
FIG. 20D is a sectional side elevation view corresponding to FIG. 20C, further illustrating details of the operation of the system.

FIGS. 20A to 20D show an alternate embodiment in which a sliding suture retainer 28B is used to trap the suture in the device. An elongated member (e.g.: a hollow shaft) 25 is provided with a tubular cutting member 60 received therein. Suture retainer 28B is received within tubular cutting member 60. Suture retainer 28B is slidable within elongated member 25. Suture retainer 28B further includes a groove 26B (shown in dotted lines in FIG. 20B) passing therethrough. When suture retainer 28B is retracted (moved proximally) to the position shown in FIG. 20A, a suture S is then received therein as shown. (For clarity of illustration, only a single suture is shown. It is to be understood that a typical use of the present invention will instead have a pair or loop of suture passing therethrough.) After suture S is received within the device, suture retainer 28B is then advanced distally to the position shown in FIG. 20B, thereby locking the suture within the device. Thereafter, as shown in FIG. 20C, cutting member 60 is distally advanced to sever the suture between the distal end 62 of the cutting member 60 and a proximal edge 52 or other flat face or suitable anvil portion (FIG. 20D) of fitting 50.

In various optional embodiments of the present invention, the present invention includes systems that dispense an agent at a location adjacent to where the suture is severed, such as the distal end of the device. In preferred embodiments, the agent may comprise an anti-infective agent, a coagulant, or a tissue glue, but the present invention is not so limited.

In accordance with the present invention, a cavity may be provided in the suture trimmer which is adapted to receive the agent therein. As will be shown, such cavity may comprise a tube or lumen passing through (or simply adjacent to) the suture retainer. In addition, the cavity adapted to receive the agent may comprise a delivery tube passing through a portion of the handle of the device. In alternative embodiments, the cavity may also simply comprise an agent storage chamber in the handle of the device. In further alternative embodiments, the cavity may also comprise a removable agent delivery cartridge which is inserted into the device.

Figure 21:
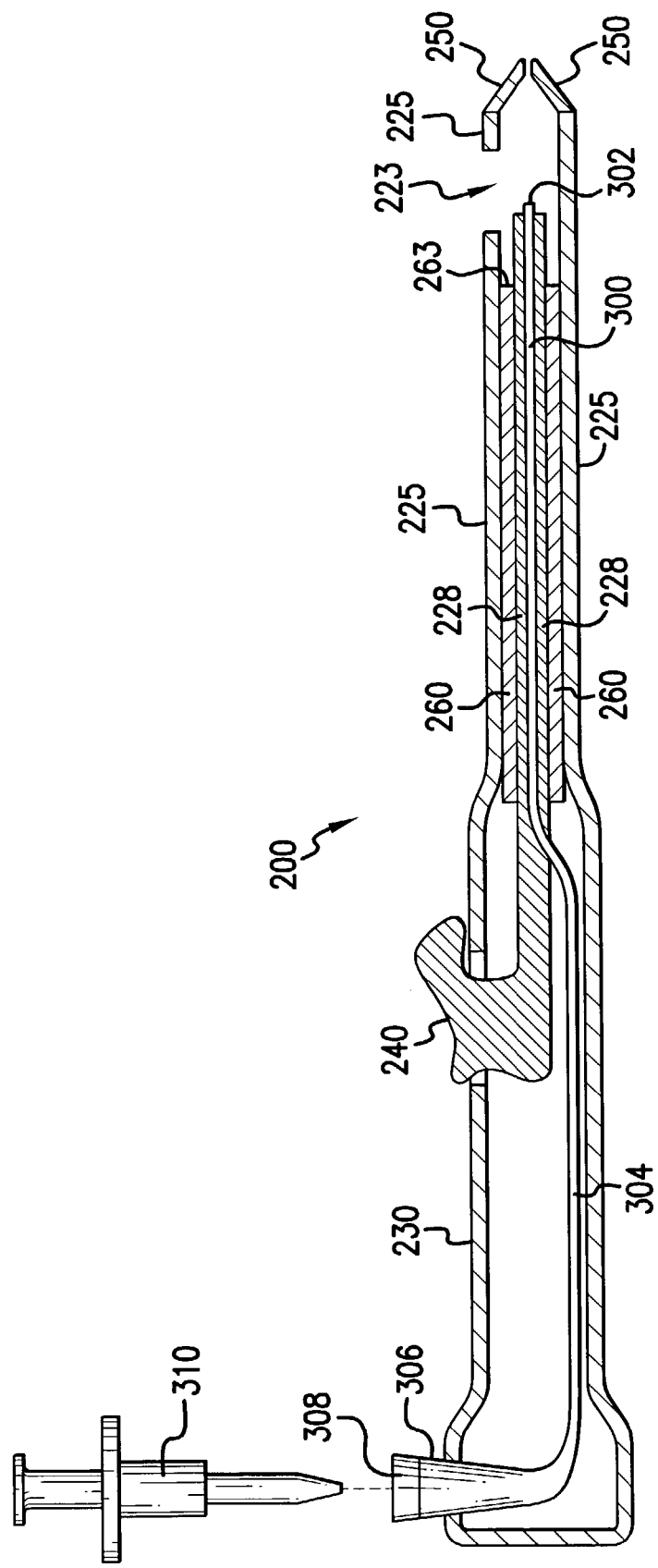
FIG. 21 is a schematic sectional side elevation view of an embodiment of the invention configured to dispense an agent at or near the location where the suture is severed.

Referring first to FIG. 21, a schematic illustration of a first embodiment of the invention which is configured to dispense an agent is provided, as follows. Suture trimmer 200 includes an elongated member 225 and a handle 230. Within elongated member 225 is disposed a tubular cutting member 260 having a distal cutting end 263. A fitting 250 is attached to the distal end of elongated member 225. Within cutting member 260 is disposed a suture retainer 228. In different embodiments, suture retainer 228 may either be rotated or be distally advanced by the operation of lever 240 to lock a suture into the device (similar to the above described operation of suture retainer 28). It is to be understood that elongated member 225, handle 230, lever 240, cutting member 260, suture retainer 228 operate in the same ways as the various above described embodiments of the elongated member, handle, lever, cutting member, suture retainer, etc. Moreover, for clarity of illustration, internal biasing devices and mechanical actuators have been omitted from FIGS. 21 to 24. Such internal biasing devices and actuators are provided and operate in the same manner as was described above.

FIG. 21 illustrates an embodiment of an agent delivery system, as follows. A tube 300 is disposed within suture retainer 228. Tube 300 has an open distal end 302 through which the agent is dispensed. Thus, the agent is dispensed at a location which is close to, or adjacent to, or simply near, the location where the suture is severed by the cutting member. In various embodiments of the invention, suture retainer 228 may either be advanced distally/retracted proximally or be rotated by actuating lever 240 on handle 230 using various mechanisms described herein.

A portion of tube 300 which passes through handle 230 includes an agent delivery tube 304. An inlet port 306 is provided in handle 230. Inlet port 306 may include a one-way check valve or luer connector 308. Thus, an operator is able to inject agent into agent delivery tube 304 by way of a syringe 310 (or other suitable delivery tube). In this embodiment, the operator is free to choose which agent is used (thus selecting from a variety of different agents pre-stored in various syringes or cartridges).

In the various embodiments where suture retainer is slidably moved or rotated within the device, tube 300 may remain stationary with suture retainer 228 sliding back and forth or rotating thereover. Alternatively, tube 300 may be replaced with a lumen passing through the suture retainer.

Figure 22:
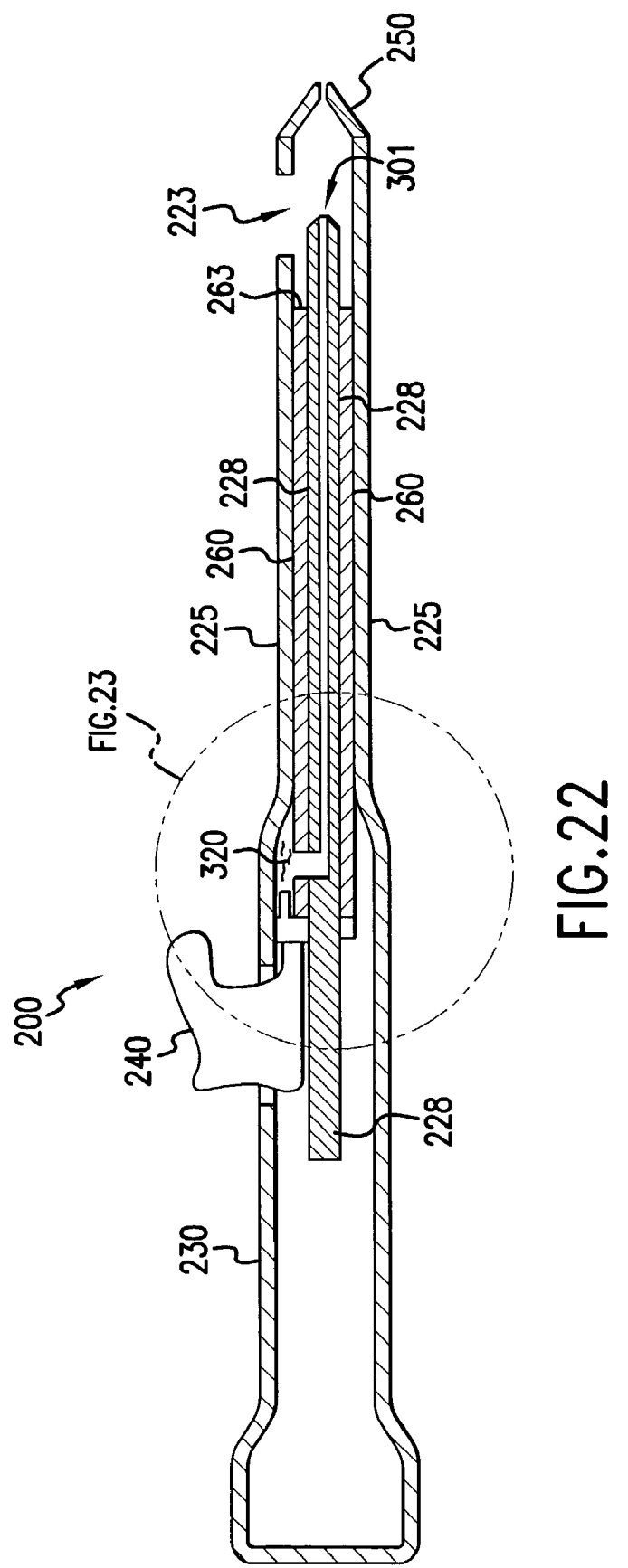
FIG. 22 is a schematic sectional side elevation view of an alternate embodiment of the invention configured to dispense an agent at or near the location where the suture is severed.
Figure 23A:
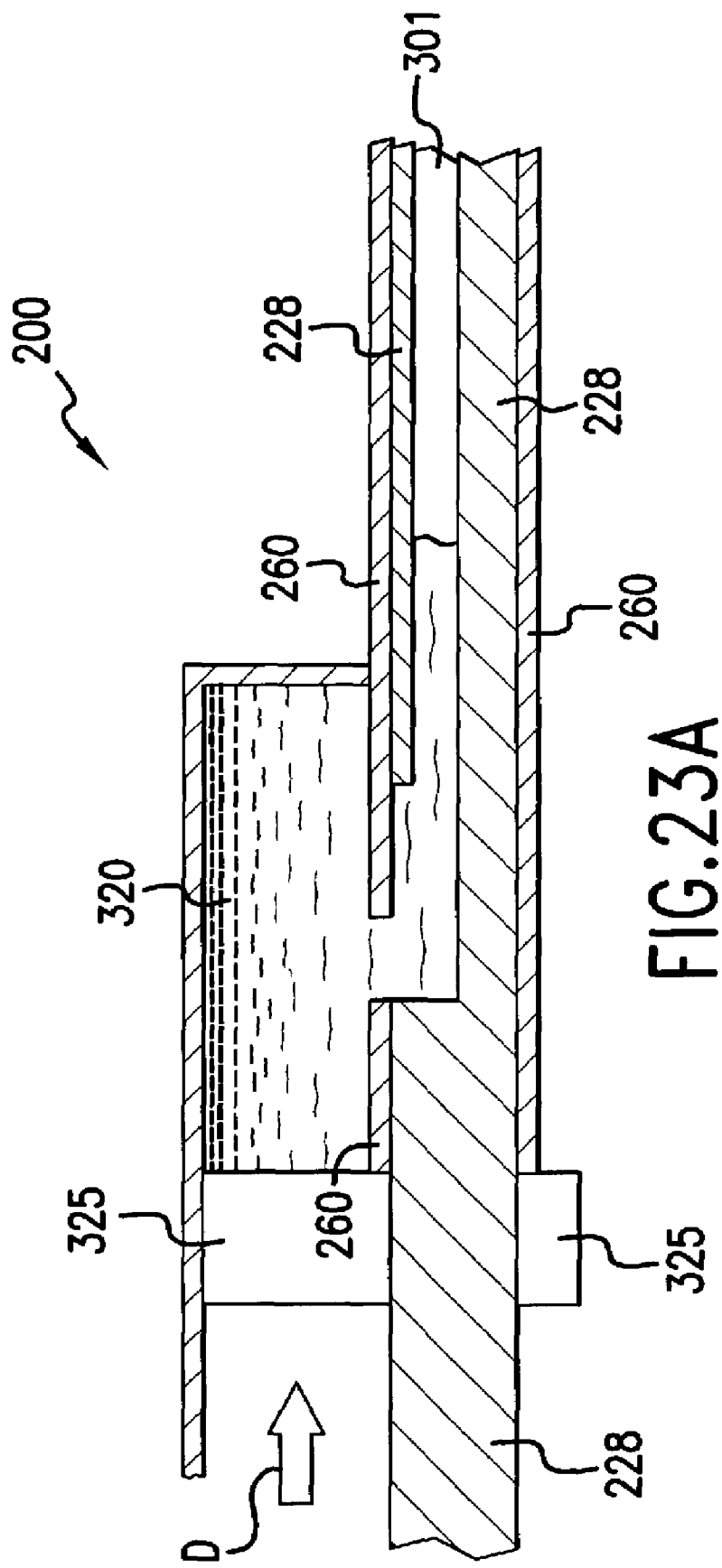
FIG. 23A is an enlarged view of a portion of the device shown in FIG. 22 prior to dispensing the agent.

FIGS. 22 to 23B illustrate an embodiment of the invention in which the agent is pre-stored in a chamber in the handle of the device. In this embodiment, the cutting member is preferably actuated at the same time that the agent is dispensed. Specifically, the agent is pre-stored in a chamber 320. A lumen 301 passes through suture retainer 228. Suture retainer 228 is received within cutting member 260. As shown schematically in FIGS. 23A and 23B, a plunger 325 is pushed distally in direction D thereby simultaneously advancing cutting member 260 while squeezing agent from chamber 320, out through the distal end of lumen 301. Thus, the agent may be dispensed at the location where the suture is severed at the same time as the cutting member severs the suture.

Figure 24:
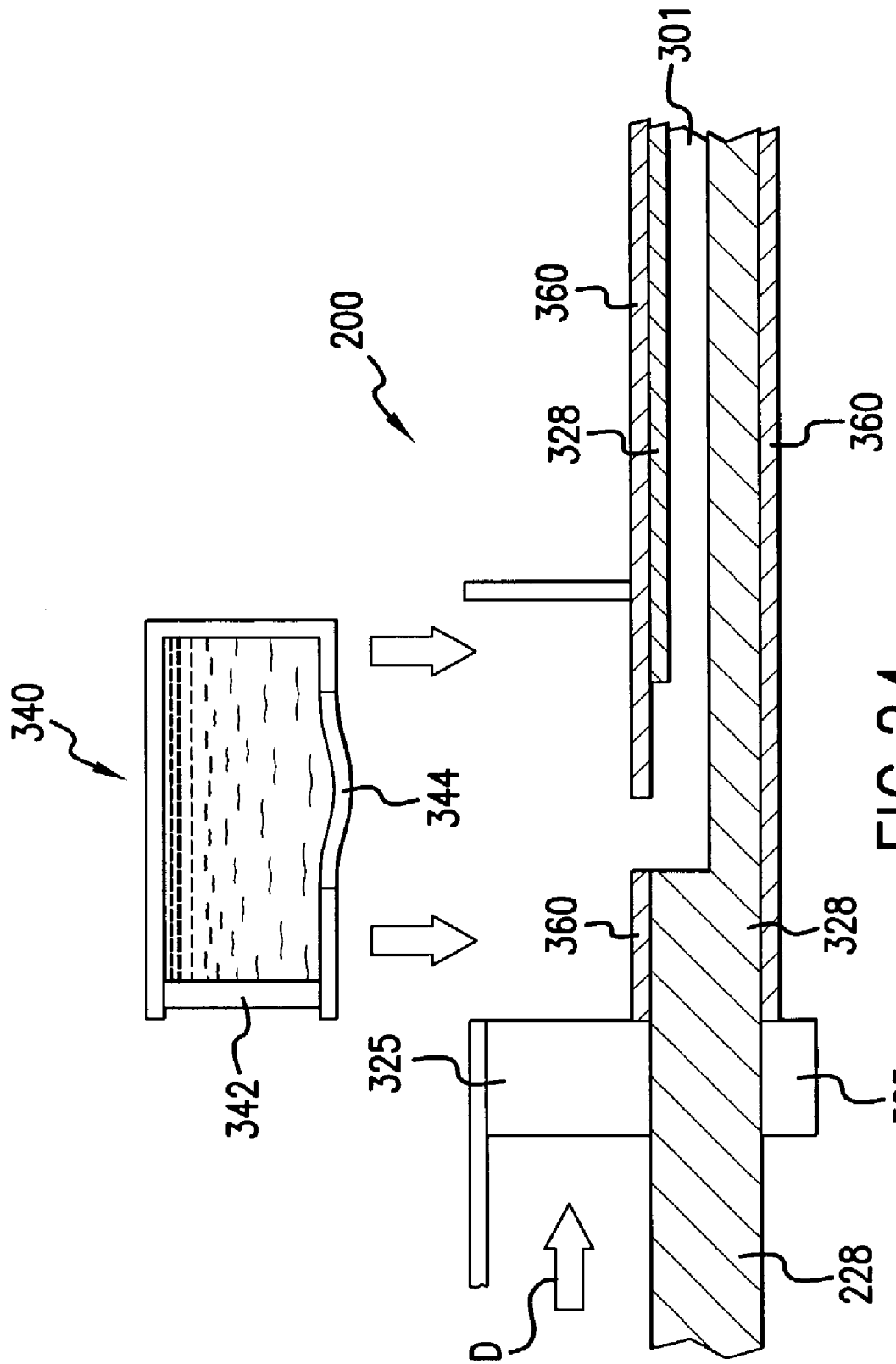
FIG. 24 is a view similar to FIG. 23A, but wherein a removable cartridge filled with the agent is instead inserted into the device.

FIG. 24 is a schematic view corresponding to FIGS. 22 to 23B, but instead showing a removable cartridge 340 pre-filled with a suitable agent. When cartridge 340 is inserted into suture trimmer 200, plunger 325 is positioned to compress cartridge 340, for example, by moving cartridge wall 342 in distal direction D. Cartridge 340 may further comprises a removable or tear-away portion 344 which, when ruptured or removed, permits the agent to be squeezed into lumen 301 as cartridge 340 is compressed.

It is to be understood that FIGS. 23A to 24 are schematic drawings, and are thus only meant only to illustrate the operating principles of the invention. Actual internal operating mechanisms may vary from those illustrated herein. As such, different internal mechanisms which achieve the same results are contemplated, all keeping within the scope of the present invention. Also, additional components may be included. For example, additional actuators and levers (not shown) may be included to control the movement of the suture retainer, cutting member and plunger, or to puncture or otherwise open a cartridge to release an agent.

Figure 25:
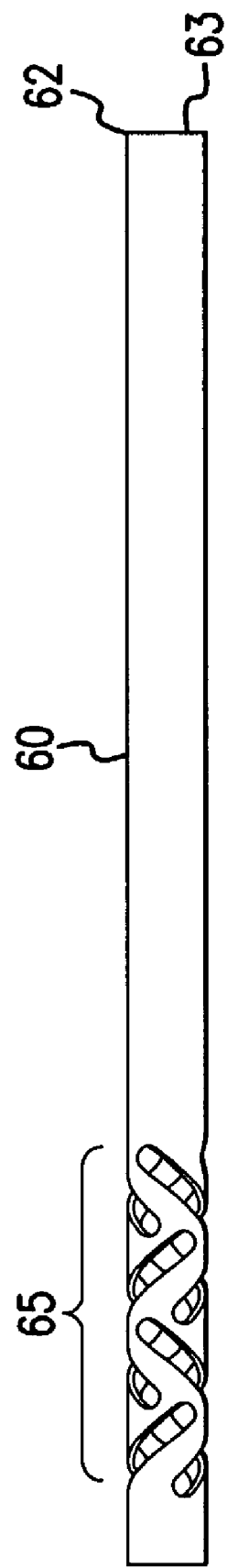
FIG. 25 is a side elevation view of an embodiment of the cutting member including optional force absorbing features.

FIG. 25 shows an embodiment of the cutting member in which the cutting member further includes force absorbing features 65. In particular, the force absorbing features comprise a series of laser cut holes near the proximal end of cutting member 60. Holes 65 are configured to give cutting member 60 the ability to deform slightly along its length. Therefore, when distal cutting edge 63 severs the suture (against either the suture retainer or the fitting) the portion of cutting member 60 that includes holes 65 will absorb some of the cutting force, thereby providing overall smoother device operation.

Figure 26:
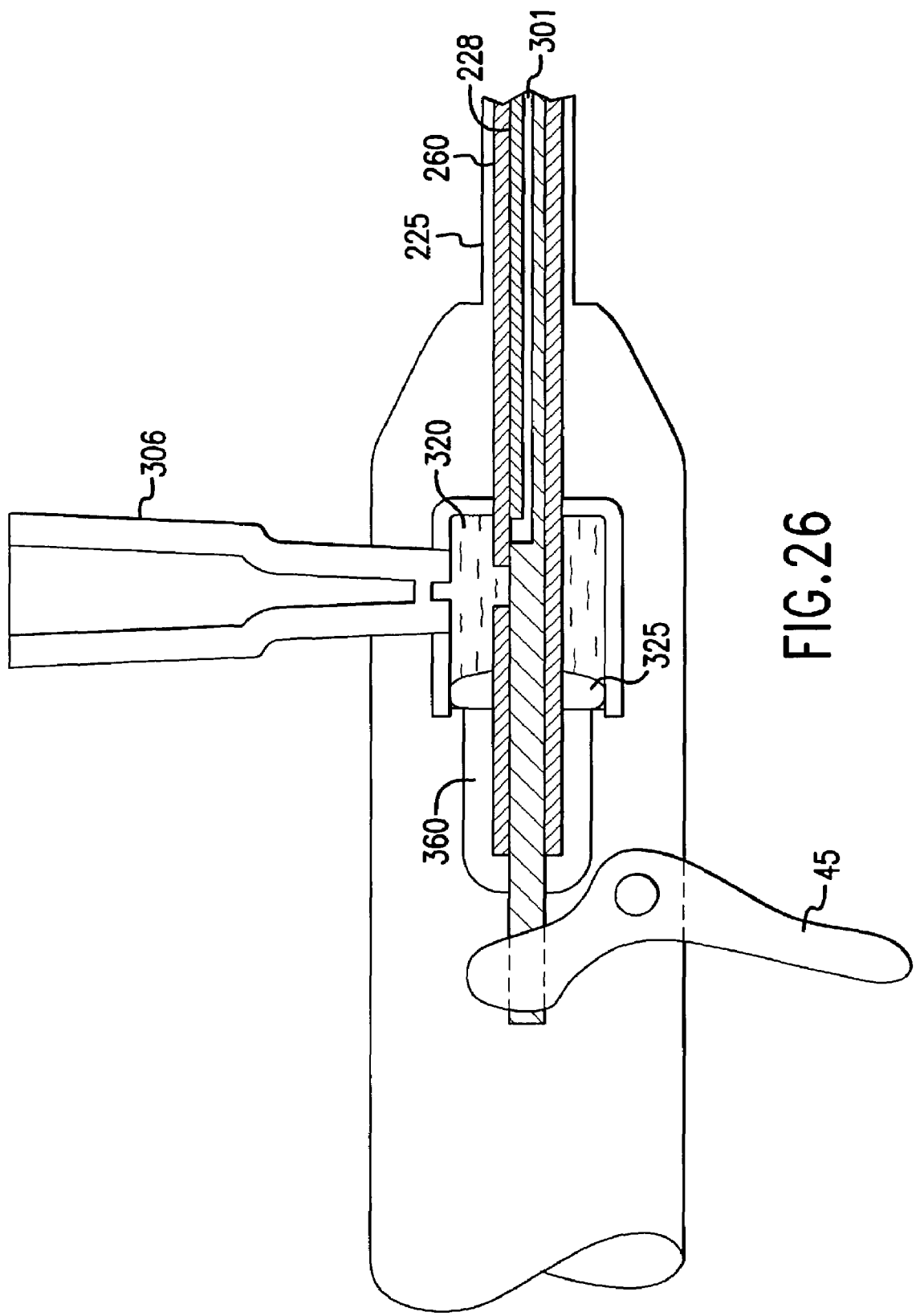
FIG. 26 is a sectional side elevation view of an embodiment of the invention having an annular shaped agent chamber, an annular shaped plunger and an annular shaped bushing.

FIG. 26 shows an embodiment of the invention in which chamber 320 is annular in shape. Plunger 325 is also annular in shape. Plunger 325 is pushed into chamber 320 by an annular shaped bushing 360. In this particular embodiment, bushing 360 is moved distally by depressing lever 45. Alternative configurations and actuation mechanisms are possible, all keeping within the scope of the present invention. For example, suture trimmer 228 may either be a rotating or sliding suture retaining mechanism as described above.

As further shown in FIG. 26, inlet port 306 may be positioned such that it enters directly into chamber 320 (thus avoiding long fluid tubes or conduits within the handle of the device).

Figure 27:
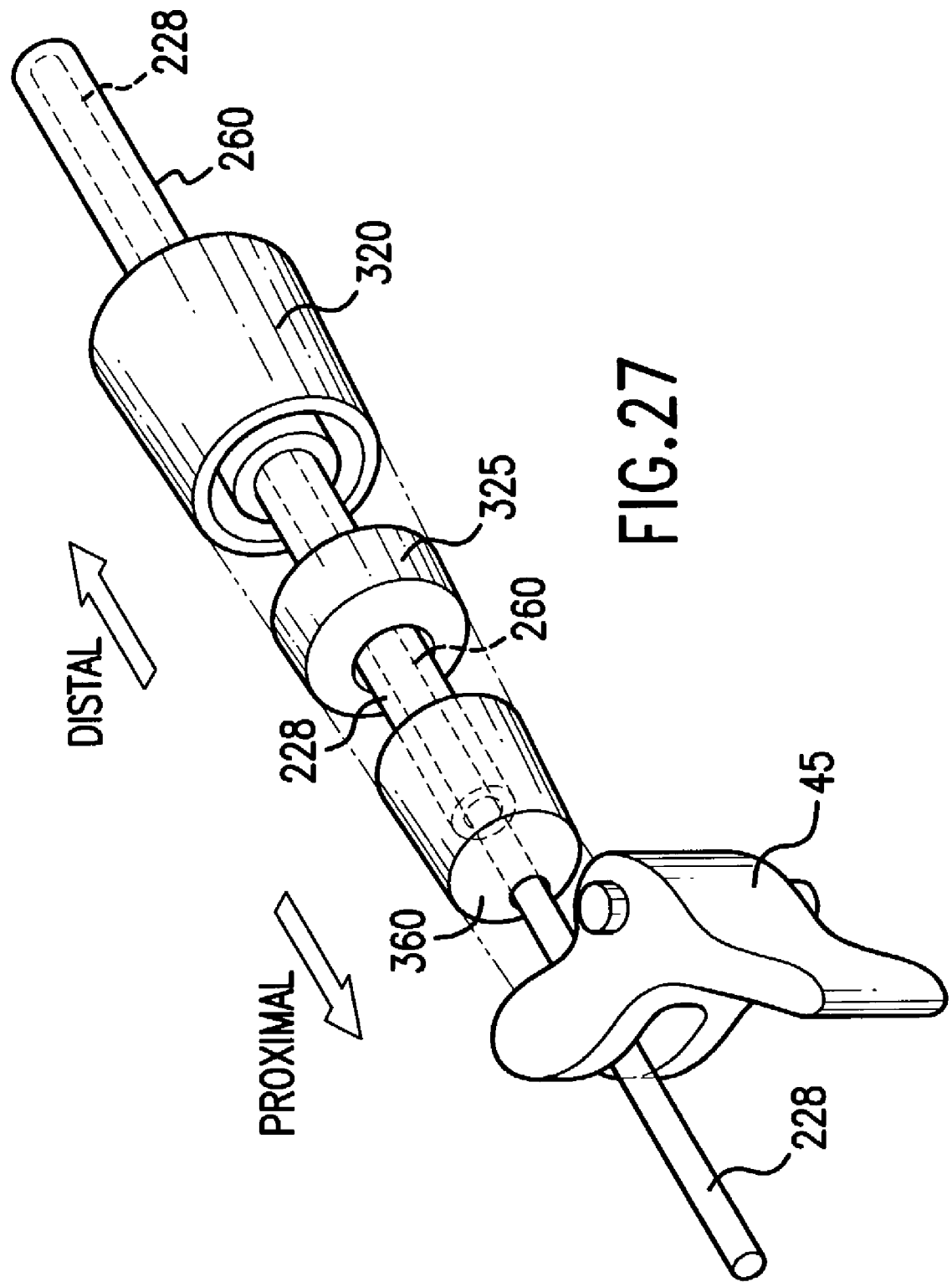
FIG. 27 is an exploded perspective view of various components shown in FIG. 26.
Figure 28:
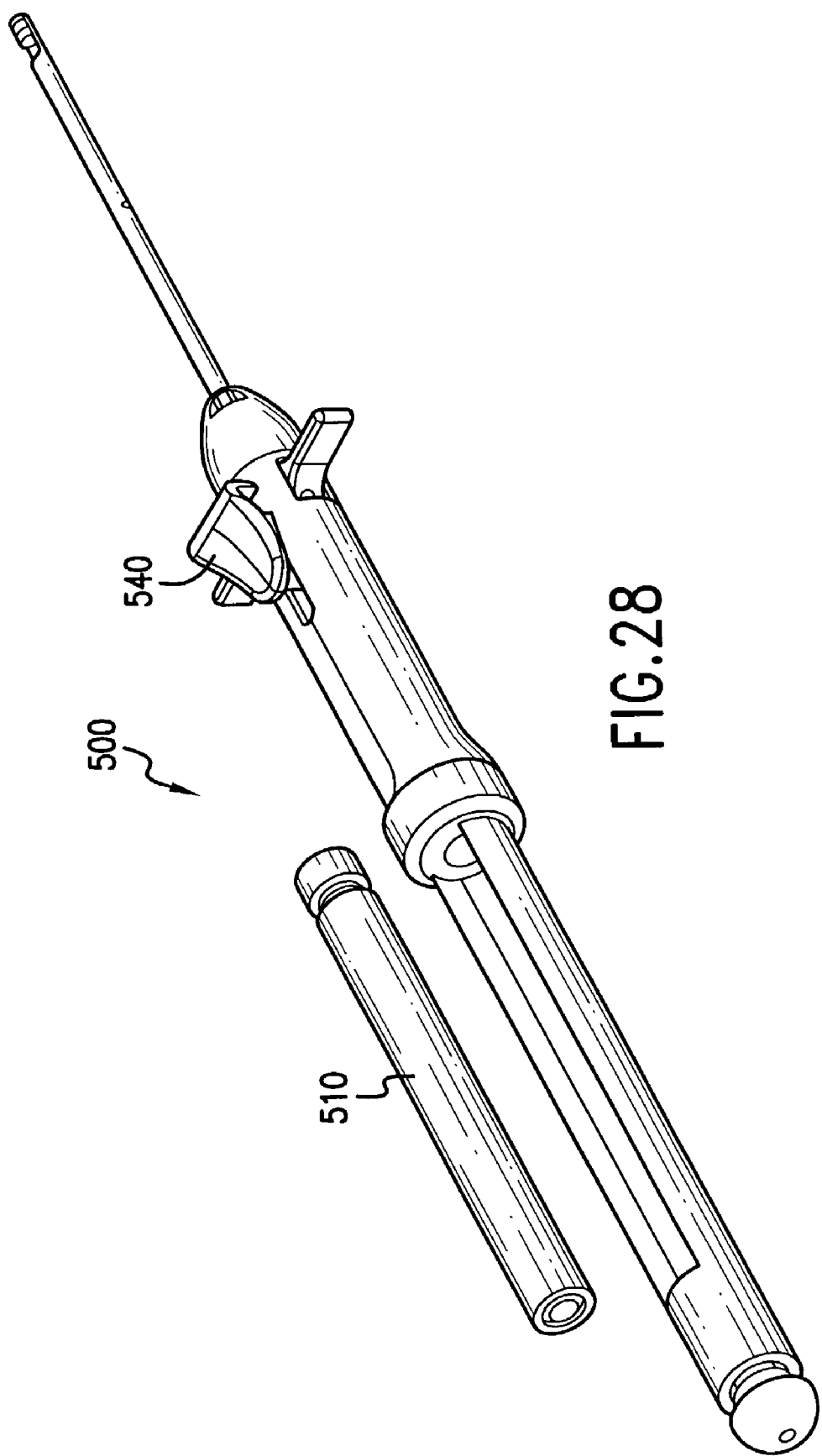
FIG. 28 is a perspective view of an alternate embodiment of the invention adapted to receive an agent cartridge therein.

FIG. 27 shows further details and shapes of the components shown in FIG. 26. In this particular embodiment, the bushing 360, plunger 325 and chamber 320 are shown in an exploded view. Actuating lever 45 pushes bushing 360 which in turn pushes plunger 325 into cavity 320. As was shown in FIG. 26, agent squeezed out of cavity 320 then passes through an opening in cutting member 260 and out through a lumen 301 in suture retainer 228. As can also be seen, cutting member 260 and plunger 325 may be actuated simultaneously when bushing 360 is moved distally by actuating lever 45. Moreover, as shown in FIG. 27, lever 45 may be dimensioned so that it does not contact suture retainer 228 and thus moves independently of suture retainer 228. Also, bushing 360 and plunger 325 may also be dimensioned to slide over suture retainer 228 so that bushing 360/plunger 325 move independently of suture retainer 228.

Figure 29:
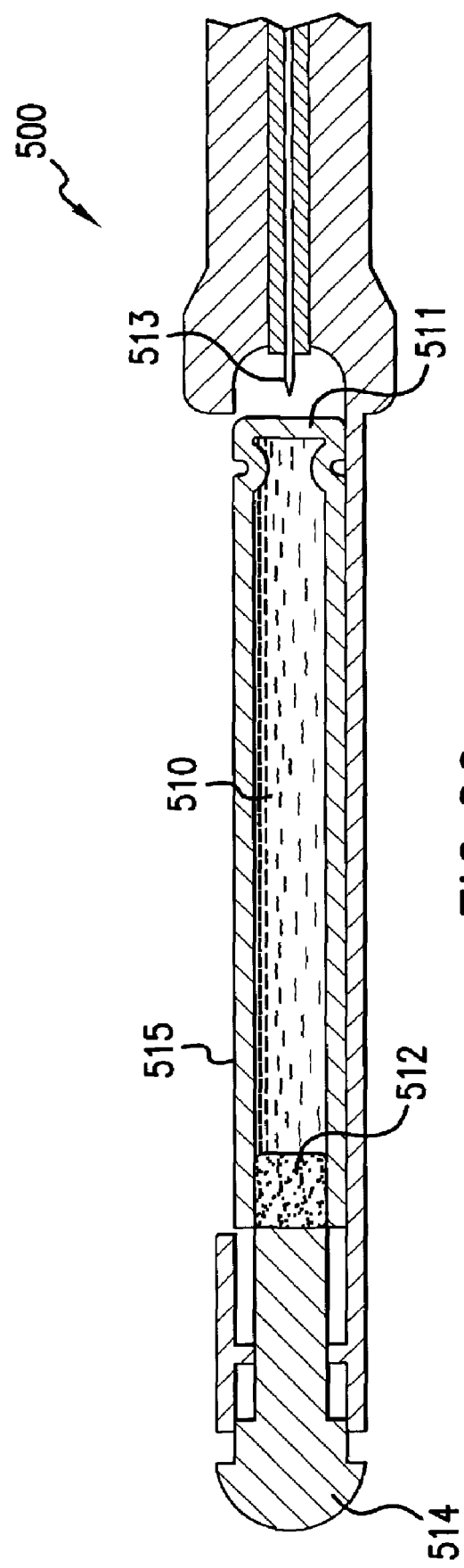
FIG. 29 is a sectional side elevation of the proximal portion of the device of FIG. 28 with an agent cartridge received therein.
Figure 30:
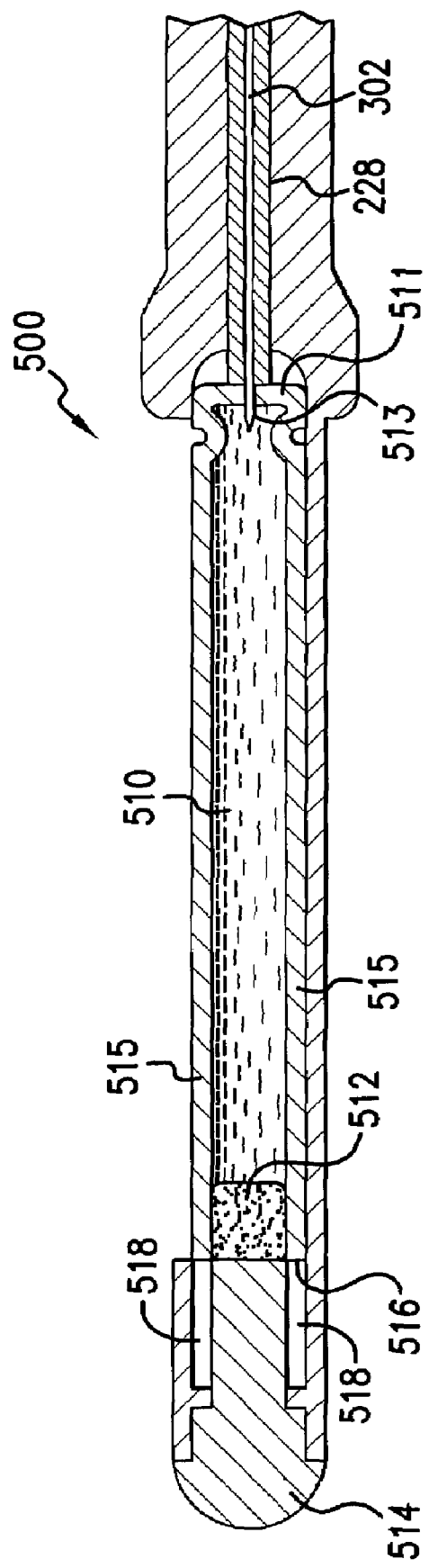
FIG. 30 corresponds to FIG. 29, but with a proximal end knob depressed, thereby both locking the agent cartridge into the device and opening the agent cartridge to fluid flow.
Figure 31:
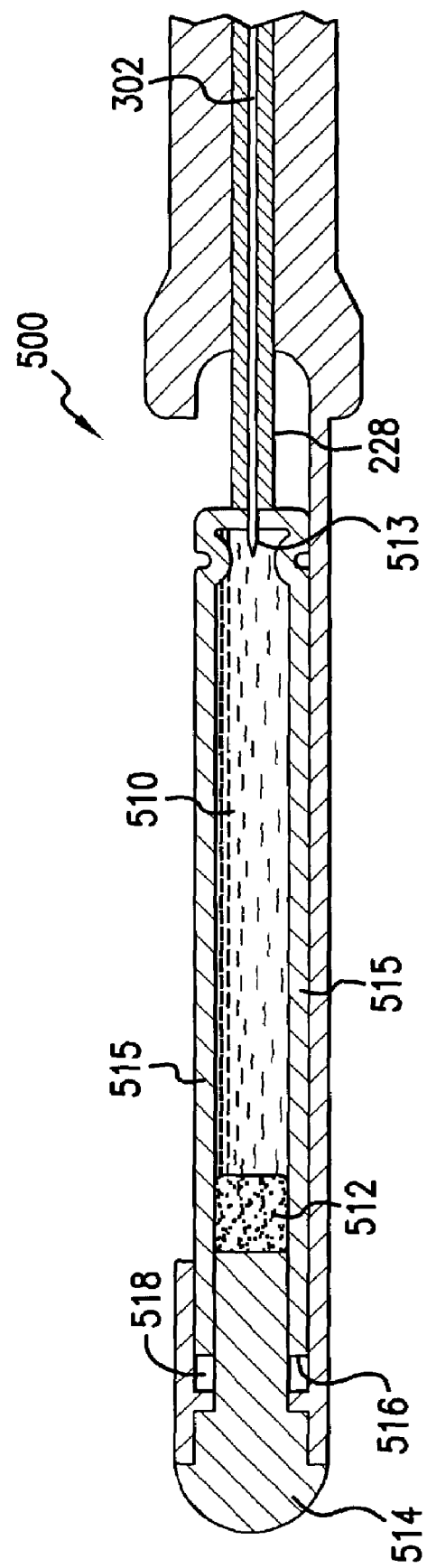
FIG. 31 corresponds to FIG. 30, but with the suture retainer moved proximally to urge agent flow out of the cartridge and through a lumen in the suture retainer.

FIGS. 28 to 31 show an alternate embodiment of the invention adapted to receive an agent cartridge into a proximal portion of the handle of the device. In particular, suture trimmer 500 is adapted to receive a cartridge 510 therein. In an exemplary embodiment, cartridge 510 is a Carpuject™ cartridge, made by Abbott Laboratories of Abbott Park, Ill. However, any suitable cartridge may also be used within the scope of the present invention. As shown in FIG. 29, cartridge 510 is first placed within a handle portion of suture trimmer 500. Cartridge 510 includes a puncturable seal 511 at its distal end and a slidable plug 512 at its proximal end. Plug 512 moves distally into tubing 515 (toward seal 511) when pressed. After an operator has selected the cartridge 510 and placed the cartridge in the body of the handle of the device (as shown in FIG. 29), end knob 514 is then depressed. By depressing end knob 514, cartridge 510 is then moved to the position as shown in FIG. 30 where cartridge 510 is moved proximally so that needle end 513 penetrates into cartridge 510. In optional preferred aspects, needle end 513 is simply connected to lumen or tube 302 which passes through suture retainer 228. Thus, cartridge 510 is now locked in position within the device and a flow path for the agent from cartridge 510 through suture retainer 228 is thereby opened. Thereafter, as shown in FIG. 31, suture retainer 228 is moved proximally (for example, by pulling back on handle 540 in FIG. 28). As can be seen, end knob 514 will keep plug 512 stationary while the outer tubing 515 (which forms the cartridge) will be pushed proximally such that its proximal end 516 is received into annular void 518. Thus, when suture retainer 228 is moved proximally, suture the agent in cartridge is forced out of the distal end of lumen 302 through suture retainer 228. The agent is dispensed at a location near where the suture is being cut. It is to be understood that the above description is only exemplary and that alternate embodiments in which different components of the invention move to receive a cartridge and to dispense agent from the cartridge are possible within the scope of the invention.

Figure 32:
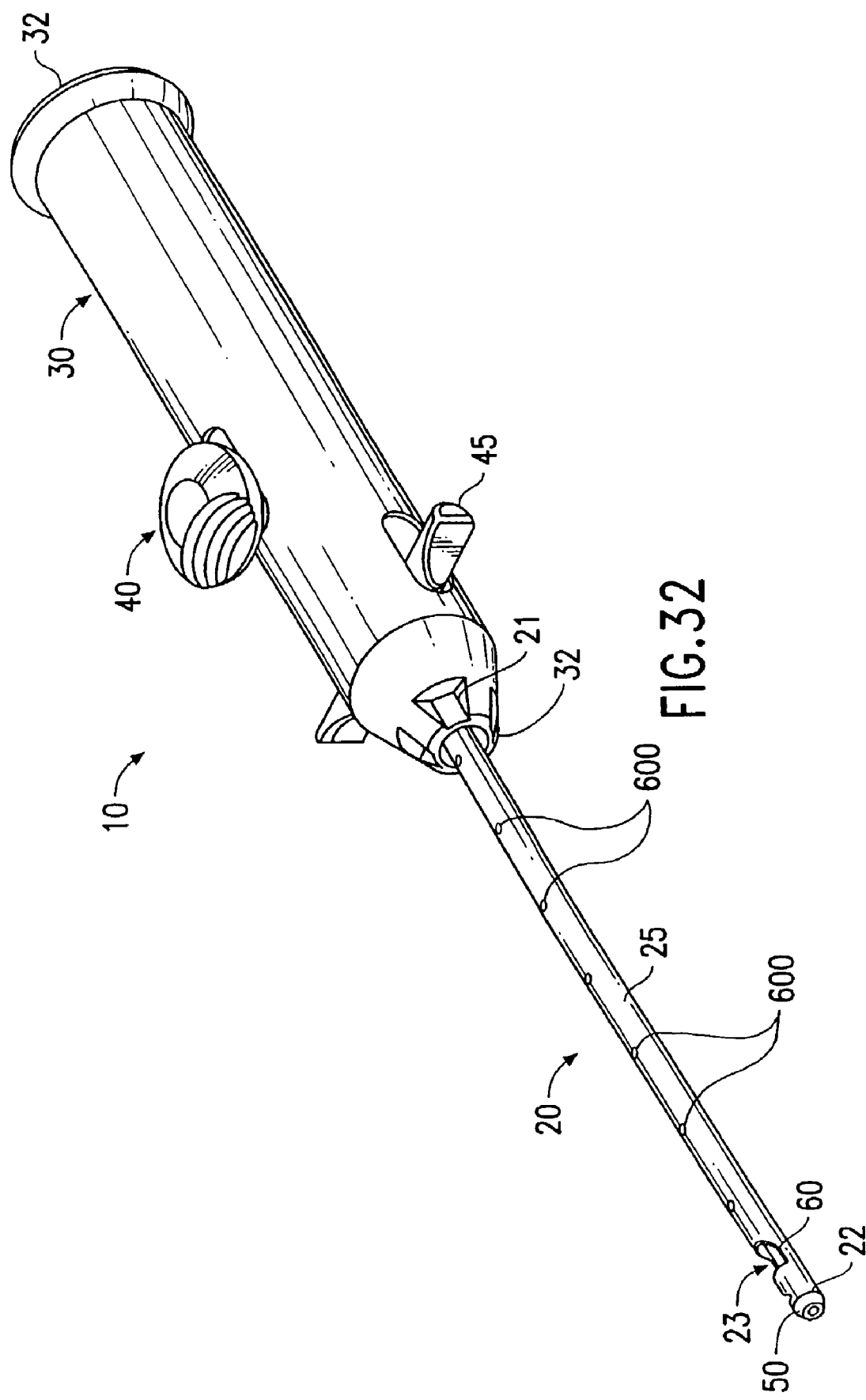
FIG. 32 is a perspective view of an alternate embodiment of the invention having a plurality of agent delivery holes spaced apart along the length of the shaft of the device.

FIG. 32 illustrates an alternate embodiment of the invention in which shaft 25 has a plurality of agent delivery holes 600 disposed along the length of shaft 25. Agent delivery holes 600 are configured to dispense an agent along the path (i.e.: tissue tract) in which the suture trimmer 10 enters the patient's tissues. Any of a variety of internal mechanisms can be provided to dispense agent directly through holes 600 in shaft 25, all keeping within the scope of the present invention. Since a suture trimmer is typically the last surgical instrument which is inserted in the patient, the present optional suture trimmer embodiment that is configured to dispense an agent along the path of the incision to the operative site is especially beneficial since anti-infective agents or coagulants or other agents may be dispensed along the path of the incision. In one optional embodiment, the series of agent delivery holes 600 may have varying diameters. The exemplary embodiment shown in FIG. 32 shows holes 600 that increase in size in the distal direction. Thus, more agent may be delivered at the distal end of the device (near where the suture is severed).

Although the present invention has been described in considerable detail with reference to certain preferred embodiments, it is contemplated that one skilled in the art may make modifications to the device herein without departing from the scope of the invention. Therefore, the scope of the appended claims should not be considered limited to the embodiments described herein.

What is claimed is:

1. A suture trimmer comprising:
a shaft having a proximal end and a distal end and an axis therebetween, the shaft having a groove formed in a side thereof, the groove being adapted to locate a suture longitudinally within a portion of the shaft and being in communication with an opening formed in the side of the shaft, the opening disposed proximal the distal end;
an agent receiving cavity in the suture trimmer within which is received an agent to be dispensed near the distal end of the shaft;
a cutting member slidably disposed within the shaft; and
a suture retainer movably disposed within the cutting member and the shaft.

2. The suture trimmer according to claim 1, wherein the cutting member is movable proximally relative to the shaft.

3. The suture trimmer of claim 1, wherein the cavity comprises a lumen passing through the suture retainer.

4. The suture trimmer of claim 1, further comprising:
a handle at the proximal end of the shaft, wherein the cavity comprises an agent delivery tube passing through the handle.

5. The suture trimmer of claim 1, further comprising:
a handle at the proximal end of the shaft, wherein the cavity comprises a chamber in the handle.

6. The suture trimmer of claim 5, further comprising:
a removable cartridge received into the chamber in the suture trimmer, wherein an agent is stored within the cartridge.

7. The suture trimmer of claim 6, wherein the removable cartridge includes a moveable wall which is adapted to be pushed into the cartridge by the action of a plunger.

8. The suture trimmer of claim 1, further comprising:
a handle at the proximal end of the shaft, wherein the cavity comprises both a chamber in the handle and lumen passing through the suture retainer, and wherein the proximal end of the lumen is in fluid communication with the chamber and a distal end of the lumen opens at the distal end of the suture retainer.

9. The suture trimmer of claim 8, further comprising:
a plunger positioned to be received into the chamber, wherein the plunger pushes the agent out of the chamber, through the lumen in the suture retainer and out of the distal end of the suture retainer when the plunger is advanced into the chamber.

10. The suture trimmer of claim 9, wherein both the cutting member and the plunger are activated simultaneously by the same actuator.

11. The suture trimmer of claim 1, wherein the handle of the suture trimmer is configured to receive a removable cartridge therein, and wherein movement of an actuator on the suture trimmer opens a flow path into the cartridge.

12. The suture trimmer of claim 1, wherein the handle of the suture trimmer is configured to receive a removable cartridge therein, and wherein movement of an actuator on the suture trimmer urges agent flow out of the cartridge.

13. The suture trimmer of claim 1, wherein the handle of the suture trimmer is configured to receive a removable cartridge therein, and wherein the suture trimmer is configured such that movement of an actuator on the suture trimmer decreases the cartridge volume while a slidable plug in the cartridge is held stationary by the handle.

14. A suture trimmer comprising:
a shaft having a groove formed in the side thereof, the groove being adapted to locate a suture longitudinally within a portion of the shaft and being in communication with an opening formed in the side of the shaft;
a cutting member movably disposed within the shaft;
a suture retainer movably disposed within the shaft, the distal end of the cutting member being movable toward an anvil portion of the suture retainer;
a cavity in the suture trimmer; and
an agent disposed with the cavity, the agent being dispensable from within the cavity, the suture trimmer being adapted to dispense the agent.

15. The suture trimmer of claim 14, wherein the suture retainer is slidably disposed within the shaft.

16. The suture trimmer of claim 14, wherein the suture retainer is rotatably disposed within the shaft.

17. The suture trimmer according to claim 14, wherein the cutting member is movable distally relative to the shaft.

18. The suture trimmer according to claim 14, wherein the cutting member is movable proximally relative to the shaft.

19. The suture trimmer according to claim 14, wherein the distal end of the cutting member is movable toward an anvil portion of the suture retainer.

20. The suture trimmer according to claim 14, wherein the cutting member is movable toward a fitting disposed in the distal end of the shaft.

21. A method for trimming suture, comprising:
disposing a free end of suture through a groove and an opening formed in a distal end of a suture trimmer, the groove being adapted to locate the suture longitudinally within a portion of the suture trimmer;

actuating a cutting member within the suture trimmer, the cutting member configured to sever the suture disposed in the opening; and dispensing an agent from the suture trimmer at a location adjacent to where the suture is severed.

22. The method of claim 21, wherein the agent is dispensed through a lumen passing through the suture retainer.

23. The method of claim 21, wherein the agent is pre-stored in a chamber in a handle at the proximal end of the shaft, the chamber being in fluid communication with the lumen passing through the suture retainer.

24. The method of claim 21, wherein the agent passes through an agent delivery tube in a handle at the proximal end of the shaft, the agent delivery tube being in fluid communication with the lumen passing through the suture retainer.

25. The method of claim 24, further comprising:
injecting the agent into the chamber through a one-way check valve.

26. The method of claim 24, further comprising:
injecting the agent into the chamber through a luer connector.

27. The method of claim 23, further comprising:
advancing a plunger into the chamber to push the agent out of the chamber in the handle and through the lumen in the suture retainer and out of the distal end of the suture retainer.

28. The method of claim 27, wherein the plunger and the cutting member are actuated simultaneously.

29. A suture trimmer comprising:
a shaft having a groove formed in the side thereof, the groove in communication with an opening formed in the side of the shaft;
a cutting member movably disposed within the shaft and movable toward a fitting disposed at the distal end of the shaft;
a suture retainer movably disposed within the cutting member and the shaft; and
an agent receiving cavity in the suture trimmer within which is received an agent to be dispensed from the shaft.

30. The suture trimmer of claim 29, wherein the suture retainer is slidably disposed within the shaft.

31. The suture trimmer of claim 29, wherein the suture retainer is rotatably disposed within the shaft.

32. The suture trimmer according to claim 29, wherein the cutting member is movable distally relative to the shaft.

33. The suture trimmer according to claim 29, wherein the cutting member is movable proximally relative to the shaft.

34. The suture trimmer according to claim 29, wherein the cutting member is movable toward a fitting disposed in the distal end of the shaft.

35. A suture trimmer comprising:
a shaft having a groove formed in the side thereof, the groove in communication with an opening formed in the side of the shaft;
a cutting member movably disposed within the shaft;
a suture retainer rotatably disposed within the cutting member and the shaft; and
a cavity in the suture trimmer; and
an agent disposed in the cavity, the agent being dispensable from within the cavity, the suture trimmer being adapted to dispense the agent.

36. The suture trimmer according to claim 35, wherein the cutting member movable distally relative to the shaft.

37. The suture trimmer according to claim 35, wherein the cutting member is movable proximally relative to the shaft.

38. The suture trimmer according to claim 35, wherein the distal end of the cutting member is movable toward an anvil portion of the suture retainer.

39. The suture trimmer according to claim 35, wherein the cutting member is movable toward a fitting disposed in the distal end of the shaft.

* * * * *